(12) United States Patent
Rashidi

(10) Patent No.: US 10,933,247 B2
(45) Date of Patent: Mar. 2, 2021

(54) LEAD WITH INTEGRATED FEATURES TO FACILITATE EXTRACTION AND ASSOCIATED METHODS OF EXTRACTION

(71) Applicant: MRM MedTech, LLC, Moreland Hills, OH (US)

(72) Inventor: Majid Rashidi, Pepper Pike, OH (US)

(73) Assignee: MRM MEDTECH, LLC, Moreland Hills, OH (US)

( * ) Notice: Subject to any disclaimer, the term of this patent is extended or adjusted under 35 U.S.C. 154(b) by 111 days.

(21) Appl. No.: 16/106,219

(22) Filed: Aug. 21, 2018

(65) Prior Publication Data

US 2019/0054303 A1   Feb. 21, 2019

Related U.S. Application Data

(60) Provisional application No. 62/548,005, filed on Aug. 21, 2017.

(51) Int. Cl.
*A61N 1/375* (2006.01)
*A61N 1/05* (2006.01)
*A61B 17/34* (2006.01)

(52) U.S. Cl.
CPC ........ *A61N 1/3752* (2013.01); *A61B 17/3468* (2013.01); *A61N 1/056* (2013.01);
(Continued)

(58) Field of Classification Search
CPC .. A61N 1/0464; A61N 1/0524; A61N 1/0578; A61N 1/0595; A61N 1/37518;
(Continued)

(56) References Cited

U.S. PATENT DOCUMENTS 3,757,375 A    9/1973  Strom
4,471,777 A *  9/1984  McCorkle, Jr. ...... A61B 17/221
                                                  294/100
(Continued)

OTHER PUBLICATIONS

Bracke, "Complications and lead extraction in cardiac pacing and defibrillation", *Netherlands Heart Journal*, V.16, Supp.1, Oct. 2008, pp. 28-31.
(Continued)

*Primary Examiner* — Tan-Uyen T Ho
*Assistant Examiner* — Charles M Wei
(74) *Attorney, Agent, or Firm* — Fay Sharpe LLP

(57) ABSTRACT

A lead assembly and associated process include a lead and an integrated feature that facilitates extraction of the lead from the associated body passage. The integrated feature in one embodiment is a sheath received between the associated body passage and received over the lead. The sheath has a first portion extending from adjacent the proximal end to adjacent the distal end of the lead, where the first portion has an inner surface facing with the lead outer surface and the first portion having an outer surface facing radially outward from the lead outer surface. A second portion of the sheath extends from adjacent the distal end to adjacent the proximal end of the lead. The second portion has an inner surface received over the outer surface of the first portion, and the second portion further having an outer surface abutting an inner surface of the associated body passage that receives the lead therein. The integrated feature is alternatively a wire, band, or spoke assembly.

23 Claims, 28 Drawing Sheets

(52) U.S. Cl.
CPC .......... *A61N 1/057* (2013.01); *A61N 1/0595* (2013.01); *A61N 1/37512* (2017.08); *A61N 1/0504* (2013.01); *A61N 1/0563* (2013.01); *A61N 2001/0578* (2013.01)

(58) Field of Classification Search
CPC .......... A61N 1/3752; A61N 2001/0578; A61B 17/3468; A61F 2/97
See application file for complete search history.

(56) References Cited

U.S. PATENT DOCUMENTS

| | | | |
|---|---|---|---|
| 4,574,800 A * | 3/1986 | Peers-Trevarton | A61N 1/056 606/1 |
| 4,732,152 A * | 3/1988 | Wallsten | A61F 2/95 604/271 |
| 4,943,289 A | 7/1990 | Goode et al. | |
| 4,988,347 A | 1/1991 | Goode et al. | |
| 5,011,482 A | 4/1991 | Goode et al. | |
| 5,013,310 A | 5/1991 | Goode et al. | |
| 5,195,978 A * | 3/1993 | Schiffer | A61M 25/0169 604/161 |
| 5,207,683 A | 5/1993 | Goode et al. | |
| 5,261,419 A | 11/1993 | Osypka | |
| 5,300,106 A * | 4/1994 | Dahl | A61N 1/05 604/164.05 |
| 5,383,924 A * | 1/1995 | Brehier | A61N 1/057 607/126 |
| 5,423,806 A | 6/1995 | Dale et al. | |
| 5,507,751 A | 4/1996 | Goode et al. | |
| 5,620,451 A | 4/1997 | Rosborough | |
| 5,632,749 A | 5/1997 | Goode et al. | |
| 5,662,703 A * | 9/1997 | Yurek | A61F 2/95 606/194 |
| 5,697,936 A | 12/1997 | Shipko et al. | |
| 5,779,715 A | 7/1998 | Tu | |
| 5,807,399 A * | 9/1998 | Laske | A61N 1/057 606/108 |
| 5,980,515 A | 11/1999 | Tu | |
| 6,478,776 B1 * | 11/2002 | Rosenman | A61B 17/3468 604/164.01 |
| 6,687,548 B2 | 2/2004 | Goode | |
| 6,712,826 B2 | 3/2004 | Lui | |
| 6,763,270 B1 | 7/2004 | Gomperz et al. | |
| 9,055,930 B2 | 6/2015 | Goode et al. | |
| 9,155,878 B2 | 10/2015 | Goode et al. | |
| 2002/0035381 A1 * | 3/2002 | Bardy | A61N 1/375 607/4 |
| 2002/0099431 A1 * | 7/2002 | Armstrong | A61F 2/97 623/1.11 |
| 2003/0212446 A1 * | 11/2003 | Kaplan | A61N 1/0587 607/129 |
| 2005/0228471 A1 * | 10/2005 | Williams | A61N 1/37518 607/126 |
| 2006/0015171 A1 * | 1/2006 | Armstrong | A61B 17/12109 623/1.12 |
| 2006/0089627 A1 * | 4/2006 | Burnett | A61B 17/12099 606/1 |
| 2008/0071341 A1 | 3/2008 | Goode et al. | |
| 2010/0249815 A1 * | 9/2010 | Jantzen | A61B 17/22031 606/159 |
| 2014/0148675 A1 * | 5/2014 | Nordstrom | A61N 1/057 600/375 |
| 2015/0105796 A1 | 4/2015 | Grace | |
| 2015/0164530 A1 * | 6/2015 | Carver | A61B 17/32053 606/129 |
| 2015/0209062 A1 | 7/2015 | Taylor et al. | |
| 2015/0258333 A1 * | 9/2015 | Carver | A61B 17/32 606/129 |
| 2016/0022303 A1 | 1/2016 | Fiser | |
| 2016/0184576 A1 | 6/2016 | Grace et al. | |
| 2020/0197205 A1 * | 6/2020 | Gage | A61F 2/966 |

OTHER PUBLICATIONS

Cleveland Clinic, "Lead Extraction", Health Library, Articles, Lead Extraction, Reviewed May 2015, 5pp.
Bracke, et al., "Pacemaker lead complications: when is extraction appropriate and what can we learn from published data?", www.heartjnl.com Heart, 2001, V.85, pp. 254-259.
Bracke, et al., "Lead extraction via the femoral artery of a left ventricular pacing lead inserted in the subclavian artery", *Pace*, Jul. 2003, Part 1, V.26, pp. 1544-1547.
Parsonnet, et al., Laser extraction of entrapped leads, *Pace*, Mar. 2001, v.24, pp. 329-332.
Manolis, et al., "Ancillary tools in pacemaker and defibrillator lead extraction using a novel lead removal system", *Pace*, Mar. 2001, V.24, pp. 282-287.
Koulouris, et al., "Intravascular lead extractions: tips and tricks", *Current Issues and Recent Advances in Pacemaker* Therapy, InTech, http://dx.doi.org/10.5772/48496, 2012, pp. 189-216.
Starck, et al., "Transvenous lead extractions: comparison of laser vs. mechanical approach", *Europace*, European Society of Cardiology, Apr. 12, 2013, pp. 1636-1641.
Mihl, et al., "A challenging lead endocarditis", *European Journal of Echocardiography Electronic Papers*, European Society of Cardiology, Nov. 3, 2009, 2pp.
Andreas, et al., "Case report: paemaker lead perforation of a papillary muscle inducing severe tricuspid regurgitation", *Journal of Cardiothoracic Surgery*, 2015, v.10, No. 39, 3pp.
Neuzil, et al., "Pacemaker and ICD lead extracton with electrosurgical dissection sheaths and standard transvenous extraction systems: results of a randomized trial", *Europace*, European Society of Cardiology, 2007, v.9, pp. 98-104.

* cited by examiner

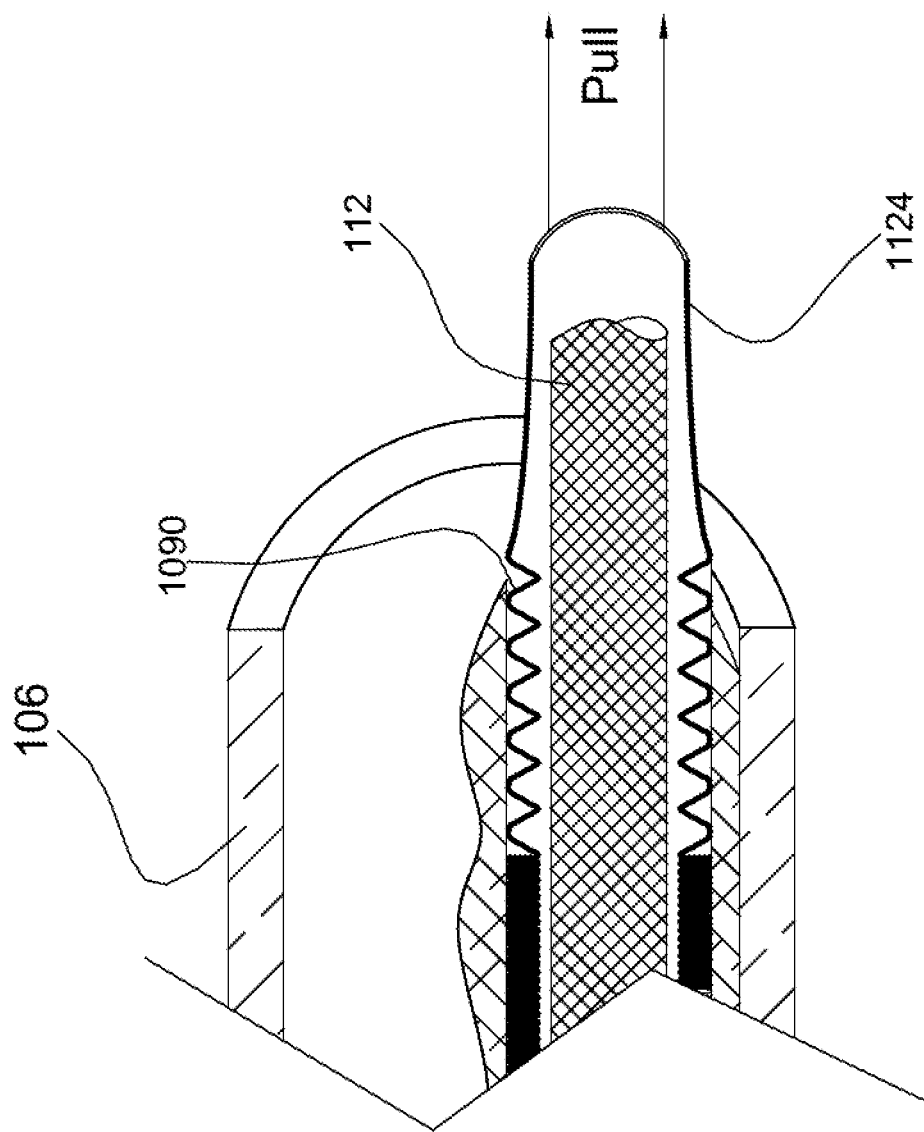

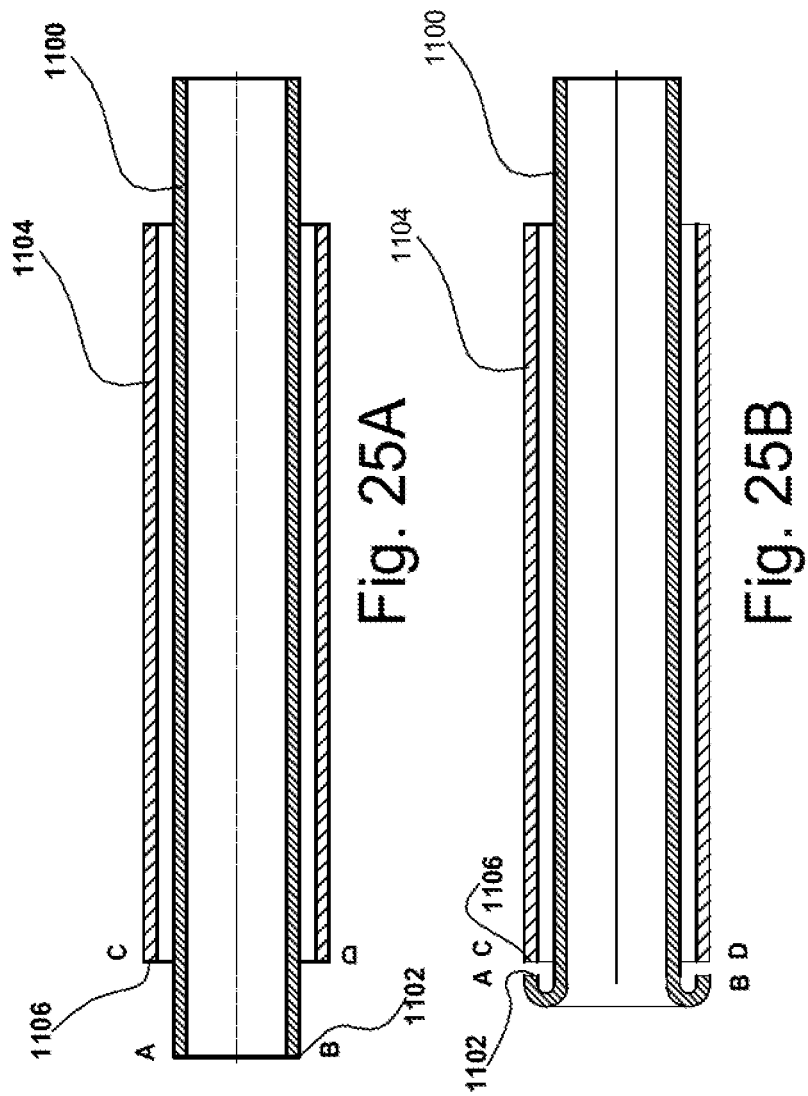

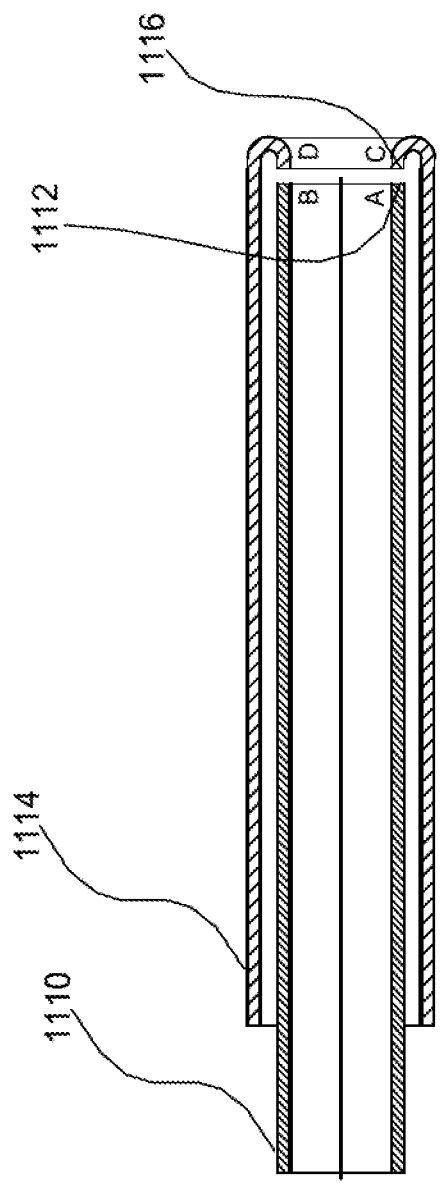
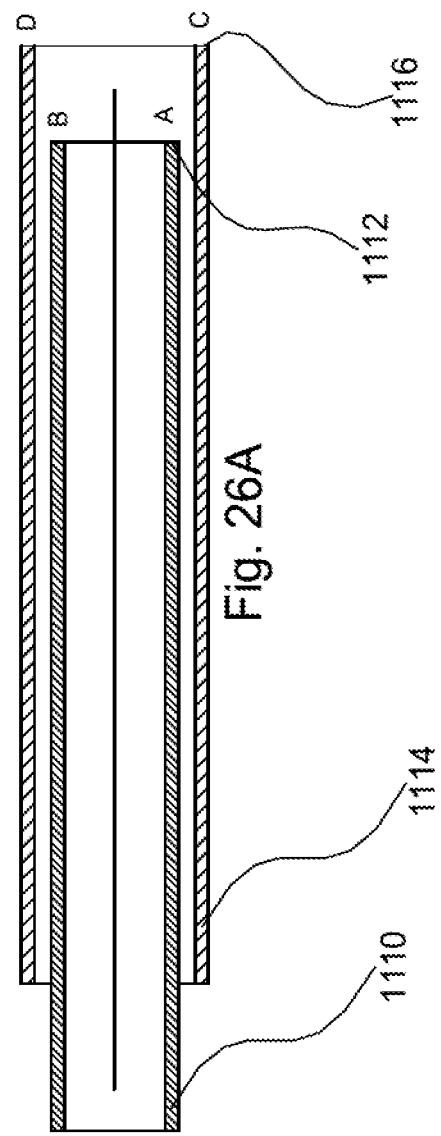
Fig. 26A
Fig. 26B

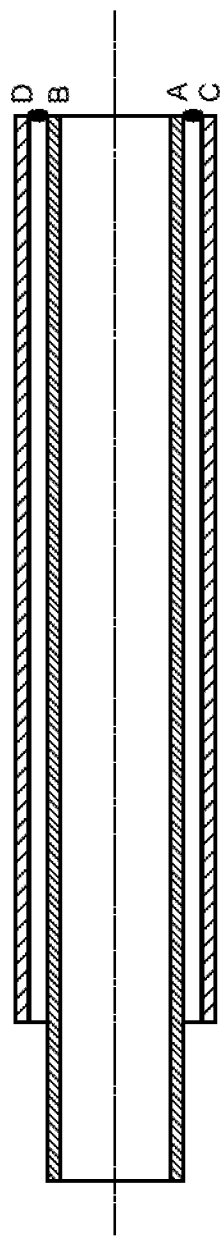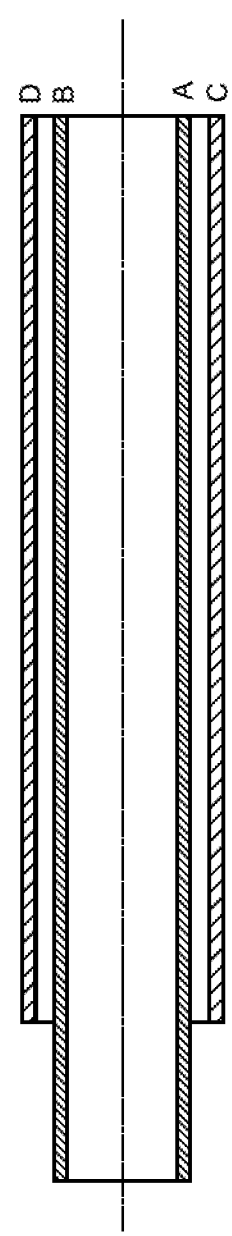

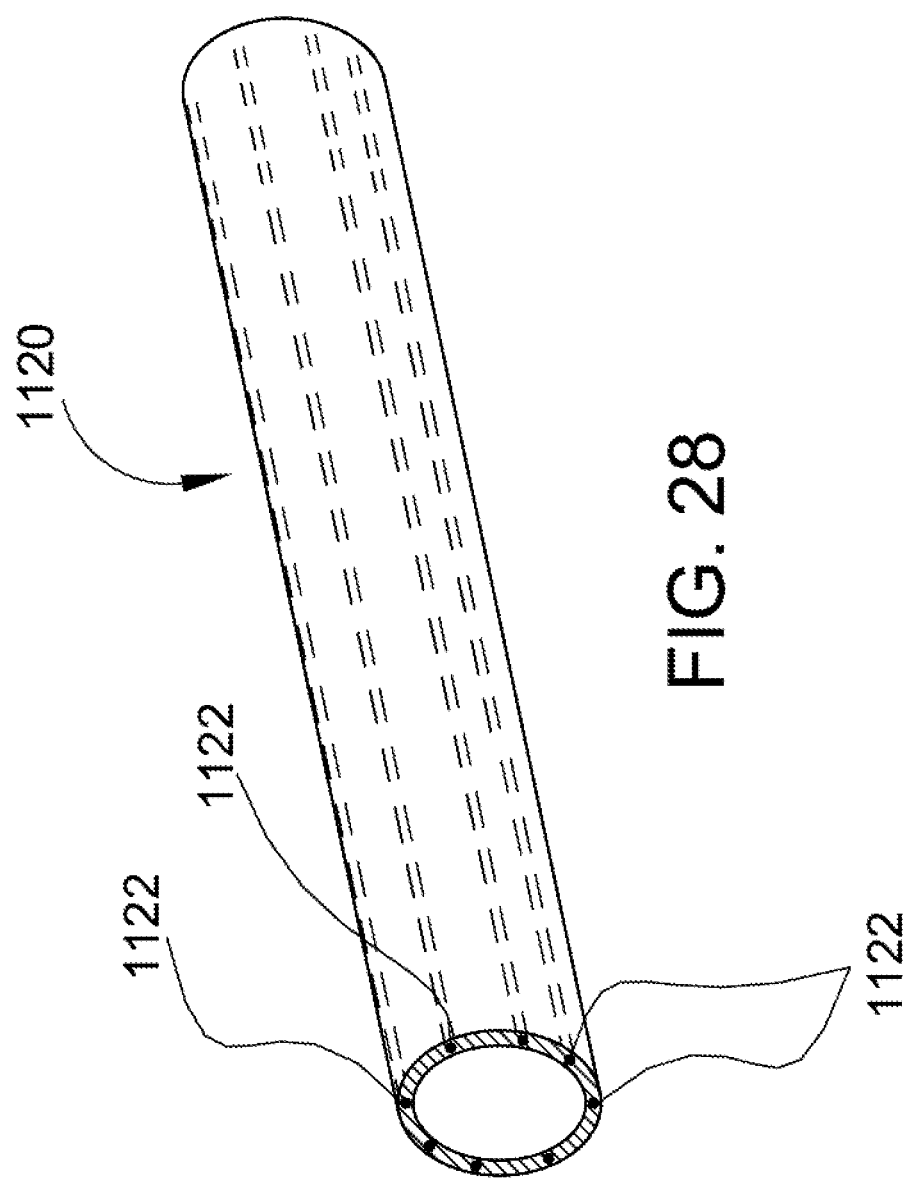

LEAD WITH INTEGRATED FEATURES TO FACILITATE EXTRACTION AND ASSOCIATED METHODS OF EXTRACTION

BACKGROUND

This application claims the priority benefit of U.S. provisional application Ser. No. 62/548,005, filed Aug. 21, 2017, the entire disclosure of which is incorporated herein by reference.

This invention relates to a lead extraction apparatus and method/process of extracting a lead from a patient where the lead is associated with, for example, a cardiac pacemaker, defibrillation system, or similar electronic device.

In cardiac pacemaker and implantable cardiac defibrillation systems, a lead or lead wire extends from and transmits an electrical signal therethrough from the pacemaker or defibrillator to the heart. It is common to use a body vessel such as a vein as a conduit for the lead wire extending from a subcutaneous implanted device, i.e., a pacemaker, to the myocardium. The distal end of the lead is connected to the heart wall in a well-known manner, e.g. by securing a helical tip provided on a distal end of the lead into the heart tissue. Of course other manners of securing the lead can be used.

Two common situations arise where it is necessary to remove the lead from the patient.

First, failure of the lead (resulting from, for example, mechanical fatigue associated with repeated flexing of the lead) would require removal or extraction of the lead from the patient. A second situation relates to infection associated with the lead. As expected, the longer the lead has been implanted in the patient, and seemingly in those situations where infection is an issue, scar tissue envelops or surrounds portions of the lead along its length because the human body is naturally trying to isolate a foreign body, i.e., the lead, by covering the site with tissue. Thus, between the proximal and distal ends of the lead, the lead may be partially or fully covered by scar tissue and this must be addressed when seeking to extract the lead from the patient. Generally speaking, both of these situations are as prevalent or likely to occur as the other, and thus both situations are equally important to address.

Two well-known commercial devices have been developed for purposes of extracting a lead from a patient.

First is an extraction device, tool, or apparatus that in one arrangement includes an elongated annular member dimensioned for receipt over the external surface of the lead. A distal end of the annular member is not a cutting edge but rather has a wedge shape for selective advancement of the wedge shape along the external surface of the lead. This advancement is intended to separate the lead from the inner lumen of the vessel. A trigger-type actuator provides for alternating counter-rotations of the annular member to provide the wedging, separating action between the lead and scar tissue as the elongated annular member is selectively advanced along the length of the lead.

Second is an extraction device, tool, or apparatus of the type that includes an elongated annular member that has a number of laser-emitting sites provided in circumferentially spaced relation on a distal end of the annular member. The laser cuts away the scar tissue from the lead as the elongated annular member is axially advanced along the length of the lead.

Each of these known extraction devices have been successfully commercialized, however each has a low probability but high-risk issue if the heart or vessel wall is damaged during the lead extraction process. Because of the high risk, a thoracic team is required to be on "standby" during such an extraction procedure in case of an emergency, even though the probability of occurrence is not high.

A need exists for an arrangement that improves on at least one or more of the above-described features, as well as still providing other features and benefits.

SUMMARY

A lead includes integrated features (herein referred to as self-extracting) that facilitate extraction, i.e., the lead is extractable without intervention of a separate device.

A self-extracting lead assembly includes an electrically conductive lead that extends between a proximal end and a distal end. In a preferred arrangement, the integrated feature includes a sheath dimensioned for receipt in an associated body passage receiving the lead and that is positioned over the lead. The sheath has a first portion extending from adjacent the proximal end to adjacent the distal end of the lead. The sheath first portion has a first surface interfacing with an outer surface of the lead. An outer, second surface of the first portion of the sheath faces radially outward from the lead outer surface.

In another embodiment, the sheath includes a second portion that extends from adjacent the distal end to adjacent the proximal end of the lead. The second portion includes an inner, first surface received over and abutting the second surface of the sheath first portion. The second portion of the lead further includes an outer, second surface that is adjacent contiguous to an inner surface of the associated body passage.

In a preferred arrangement, the first and second portions of the sheath are an integral, one-piece, continuous component where the first portion of the sheath is a continuous extension of the second portion of the sheath.

In another arrangement, the first and second portions are separately formed and subsequently joined together.

The outer surface of the first portion of the sheath merges into and becomes a continuous extension of the inner surface of the second portion of the sheath (and likewise, the inner surface of the first portion of the sheath merges into and becomes a continuous extension of the outer surface of the second portion of the sheath).

In a preferred arrangement, the sheath folds back upon itself at the junction of the first portion and second portion of the sheath.

A process of extracting the lead assembly from an associated body passage includes applying a tensile force to a first, proximal end of a first portion in order to separate the sheath from the body passage.

In a preferred arrangement, the lead assembly includes a second portion so that the folded region is urged inwardly from an inner surface of the associated body passage. The method includes selectively separating the distal end of the sheath second portion from the inner surface of the associated body passage.

The separating step includes further separating the sheath second portion from the inner surface of the associated body passage by continuing to apply a tensile force to the proximal end of the sheath first portion whereby the sheath second portion progressively separates from the inner surface of the associated body passage from the distal end toward the proximal end.

The tensile force is preferably applied over an entire perimeter at the distal end of the second sheath portion.

A primary advantage is the ability to self-extract the lead from a body passage without the use of an associated tool.

Another benefit resides in the ease with which the lead is extracted from the body passage.

Yet another advantage is the ease with which existing leads can be modified to incorporate structural features of the present disclosure.

Still other benefits and advantages of the present disclosure will become more apparent from reading and understanding the following detailed description.

BRIEF DESCRIPTION OF THE DRAWINGS

FIG. 1 is a schematic representation of an electrical lead such as a endocardial lead used in connection with a pacemaker, defibrillator, or the like, and the inclusion of a first embodiment of a.

FIGS. 23 and 24 show the sheath as a pleated or bellows-like assembly.

FIGS. 25A-25B, 26A-26B, 27A-27B illustrate two-part sheaths that are joined together.

FIG. 28 is a perspective view of another embodiment of a sheath that includes flexible, axially inextendible features added to the arrangement.

DETAILED DESCRIPTION

Figure 1:
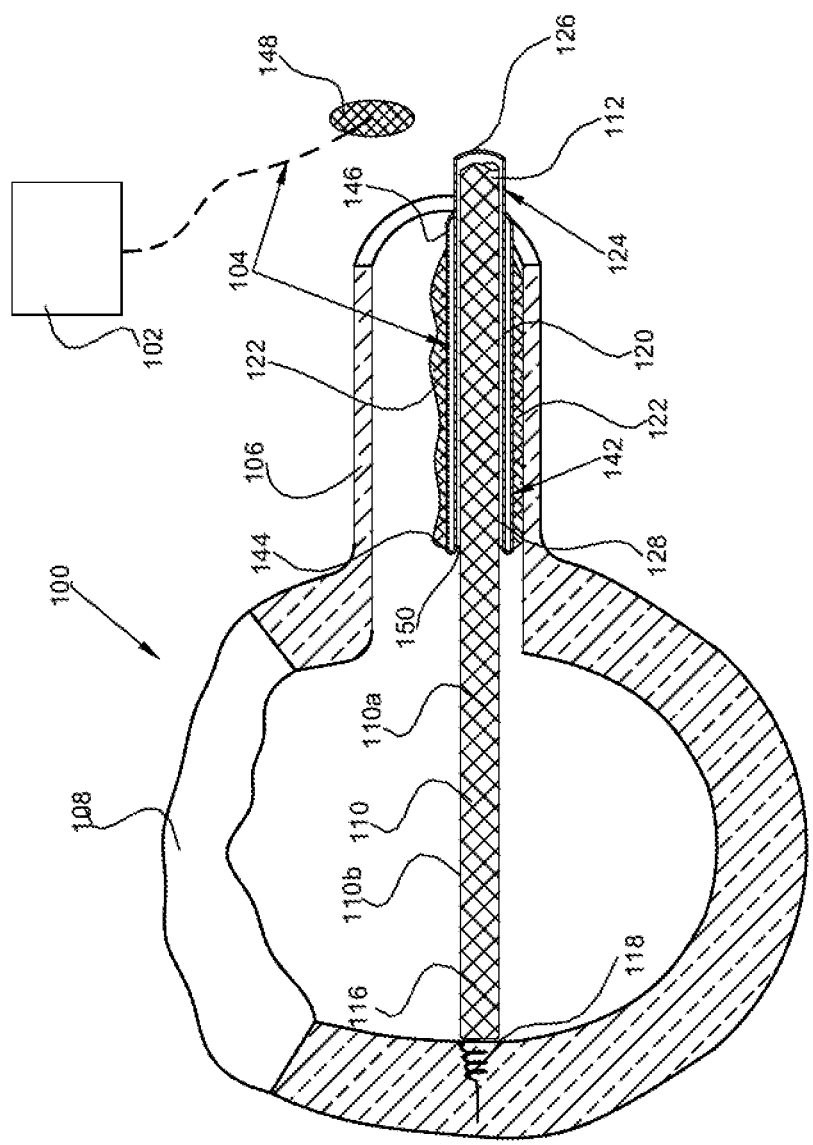
Figure 2:
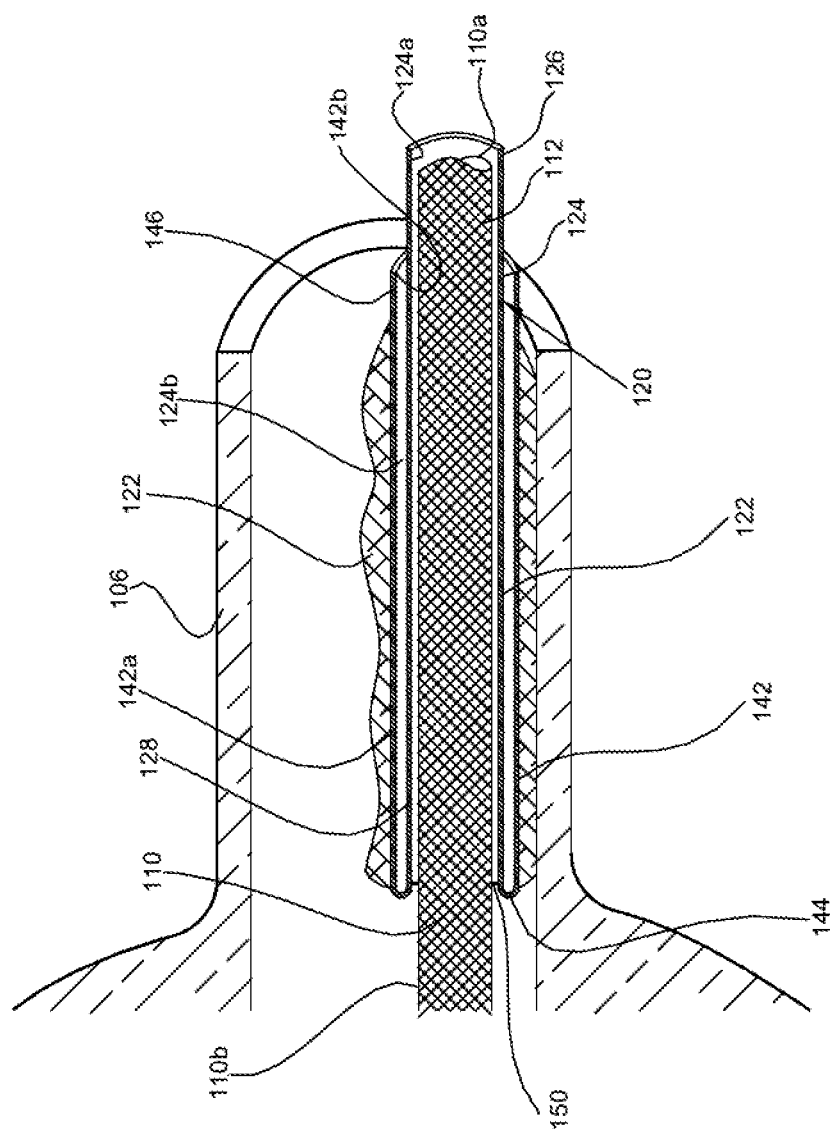
FIG. 2 is an enlarged view of the self-extracting lead assembly of FIG. 1.
Figure 3:
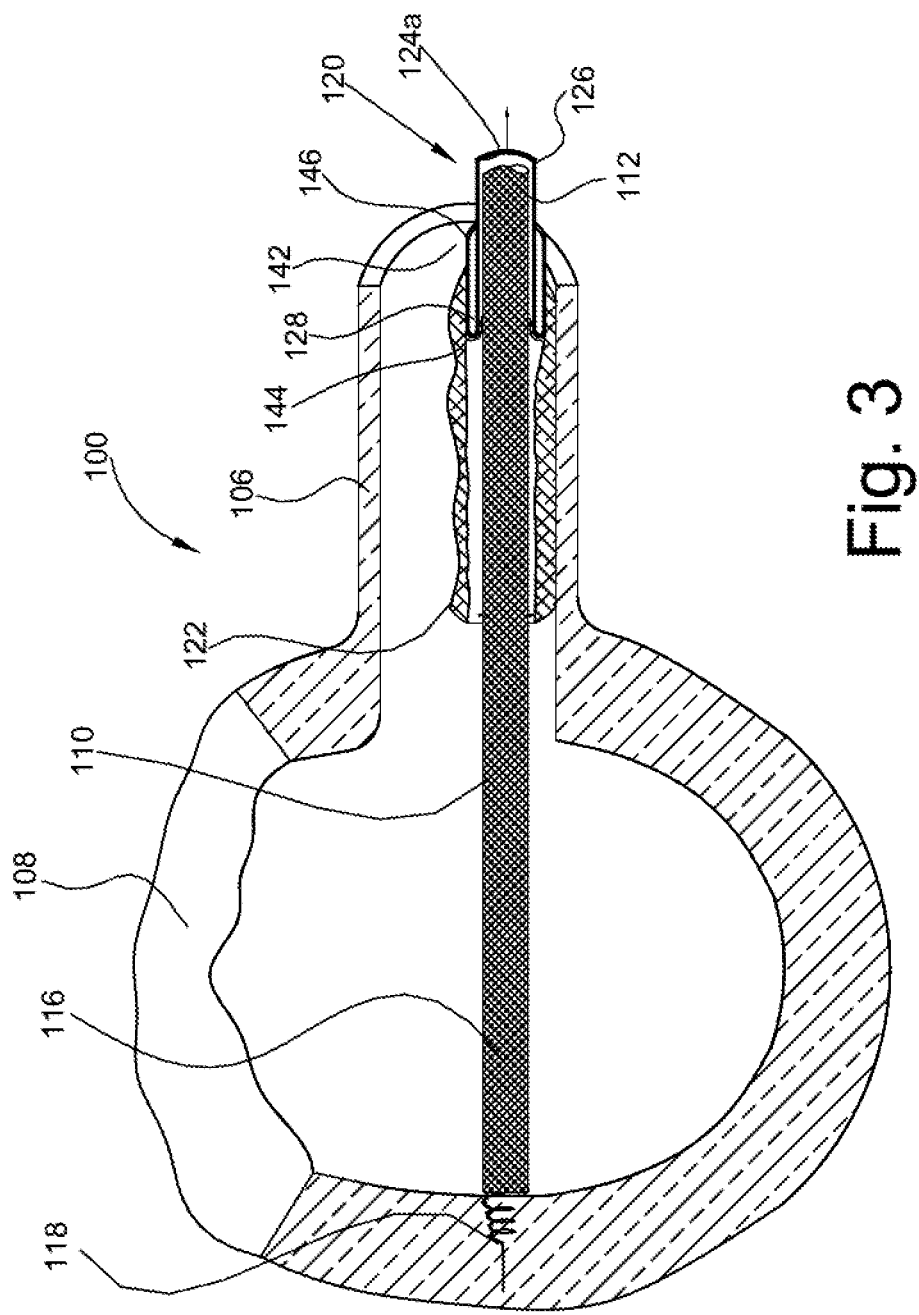
FIG. 3 is a view of the assembly of FIG. 2 with the self-extracting feature partially removed.
Figure 4:
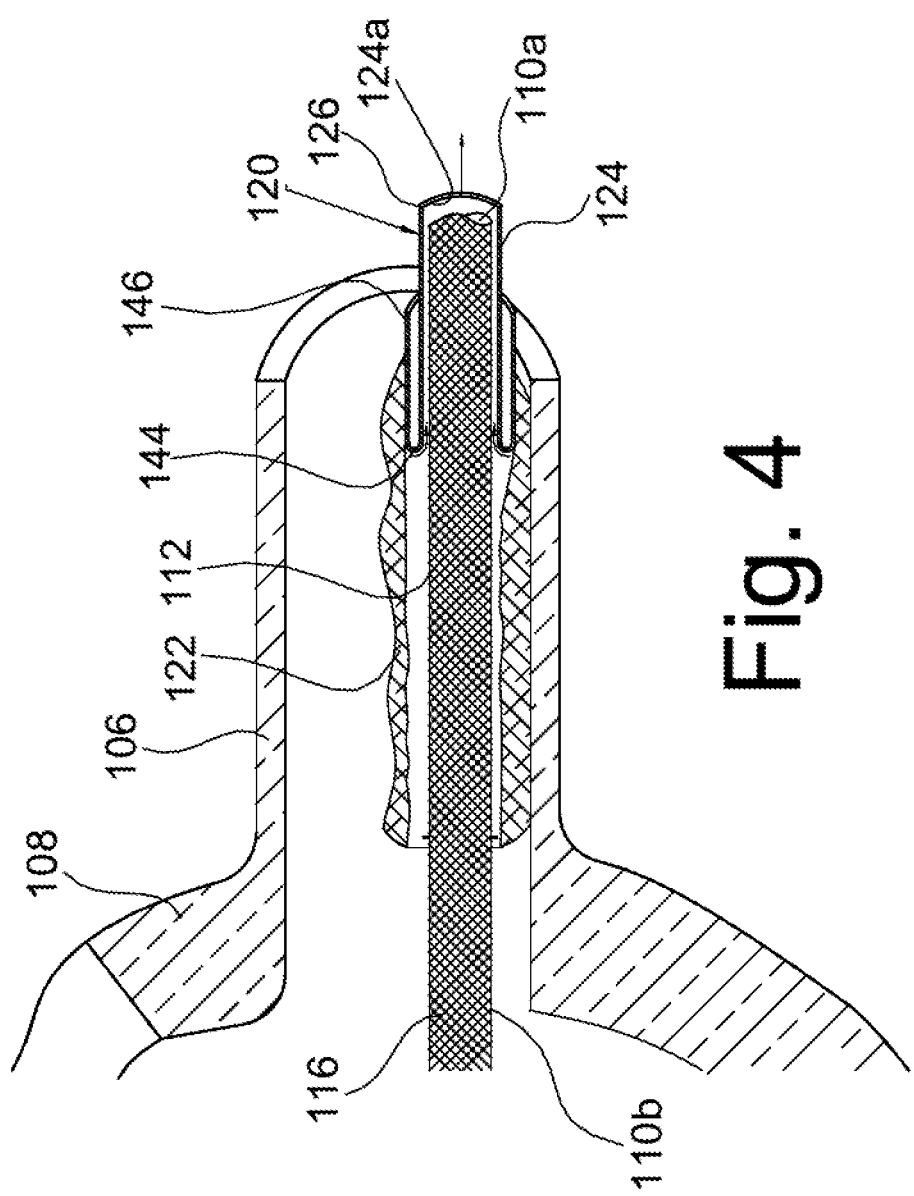
FIG. 4 is an enlarged view of FIG. 3.

New solutions are proposed, and have a common, distinct advantage of providing an extraction or separation component/tool that is integrated or incorporated into the lead, i.e., the lead is structured to include a "self-extracting" aspect.

Turning to FIGS. 1-4, there is schematically represented a first embodiment of the present disclosure in connection with a medical device assembly or system 100 that includes a cardiac stimulation device 102 (pacemaker, implantable defibrillator, etc.) from which a self-extracting, elongated lead assembly 104 extends through a body passage such as a vein 106 for connection to a heart 108. In the present disclosure, self-extracting generally refers to a structure or assembly that limits the need for specialized tools or components to separate the lead assembly from scar tissue and/or for removing/extracting the lead assembly from the body passage such as a vein 106.

More specifically, the lead assembly 104 includes a lead 110 dimensioned for receipt through the vein 106. The vein 106 extends to heart 108 whereby the lead assembly 104 may be positioned for insertion into the heart, typically a distal end of the lead threaded into a wall of the heart 108.

The lead 110 has a first or proximal end 112 that is in communication with the pacemaker 102, for example, and a second or distal end 116 that is secured to the heart. The lead 110 has an electrically conductive material or core 110a such as a thin metal wire that is typically encased within a physiologically biocompatible material such as a polymeric coating 110b. The distal end 116 has a securing structure such as a threaded end 118 for threadedly embedding the distal end into the heart 108. In this manner, electrical pulses are sent from the pacemaker 102 through the lead 110. The electrical impulses stimulate the heart 108 in a manner well known in the art. Since the general structure and function of the cardiac stimulation device 102 (pacemaker) is well known in the art, further description thereof is not required and does not form a part of the present disclosure.

There may arise instances in which it becomes necessary to remove the lead assembly 104 from the body. Over time, at least portions of the lead assembly 104 are covered by tissue, i.e., scar tissue, 122 which encases or covers the lead assembly at various regions or locations along the length of the vein 106. Removal or extraction of the lead assembly 104 has heretofore been a difficult task due to the at least partial encasement of the lead assembly by the scar tissue 122. As noted in the Background, specialized devices have been developed over the years for the distinct purpose of extracting leads from the body. Here, the lead assembly 104 is modified, specifically through addition of an integrated feature 120 that facilitates removal of the lead assembly from the body passage, and in this instance the integrated facilitating feature is carried by or incorporated into the lead assembly. In the embodiment of FIGS. 1-4, the feature is a casing or sheath 120 received over the outer perimeter surface of the conductive lead 110 to facilitate removal or extraction of the lead from the body passage.

The sheath 120 extends over substantially an entire length of the lead 110 and covers the outer perimeter or outer surface of the conductive lead 110, that is the casing or sheath is received over the polymeric coating 110b. The sheath 120 is formed from a physiologically biocompatible material, such as a polymer material, that encases the lead 110 and in the same manner as the polymeric coating of the lead, the sheath serves a variety of purposes such as (i) allowing the lead assembly 104 to be sterilized before insertion or implantation in the body, (ii) not adversely impacting the electrical pulses sent through the conductive lead, and/or (iii) being biocompatible with the body, etc.

In a first preferred embodiment shown in FIGS. 1-4, the sheath 120 is approximately twice the length of the lead 110 that the sheath encases. Specifically, the sheath 120 has a first, inner layer referred to herein as a sheath inner portion 124 (particularly an inner surface 124a of the inner portion) which surrounds or covers an outer perimeter or surface 110a of the lead 110 from a first or proximal end 126 of the sheath inner portion to a second or distal end 128 of the sheath inner portion that is disposed closer to the securing structure 118 of the lead than the proximal end 112. The sheath 120 continues in a reverse pattern, i.e., the sheath is reversed/turned back upon itself or invaginated, whereby a second or outer layer (referred to herein as a sheath outer portion) 142 surrounds or covers the inner layer 124 from a first or distal end 144 (that is a continuation of the distal end 128 of the inner layer) to a second or proximal end 146. Thus, the sheath outer portion 142 covers or is situated along an outer surface 124b of the sheath inner portion 124. It is also preferable to join the terminal, proximal end 146 of the sheath outer portion 142 to the sheath inner portion 120. For example, a suture 148 can be provided to secure the proximal end 146 of the sheath outer portion 142 to the sheath inner portion 120.

The body will naturally encase portions of the lead assembly 104 by tissue 122 forming over and covering at least portions of the lead assembly. More specifically, the tissue 122 will directly contact the sheath outer portion 142 (i.e., an outwardly facing or outer surface 142a of the sheath outer portion 142) that forms a part of the sheath 120. An inwardly facing or inner surface 142b of the sheath outer portion 142 is disposed in facing relation with the outer surface 124b of the sheath inner portion 124. As a consequence of this reverse orientation or invaginated structural arrangement of the sheath 120, the sheath inner portion 124 is interposed or forms an intermediate layer between the sheath outer portion 142 and the lead 110 so that, generally speaking, the sheath inner portion is not in direct contact with the tissue 122 that covers or encases the lead assembly 104. In this manner, the extraction process associated with the lead assembly 104 eliminates the need for a specialized extraction tool in order to remove the lead 110 from a patient.

Instead, the lead assembly 104 is introduced through the body passage/vein 106 with an exposed end (i.e., without any enclosing sheath) of the lead 110 situated in the heart 108 and the securing structure 118 threaded into the wall of the heart. The invaginated sheath 120 is secured by a frangible securing member 150 to the outer surface 110a of the lead 110 adjacent the distal end 144, i.e., that region where the inner sheath portion 124 is reversed in its orientation (reverses direction, and the outer sheath portion 142 proceeds to cover the inner sheath portion). The securing member 150 may be a circumferentially continuous attachment of the sheath 120 to the lead 110, or may be a circumferentially discontinuous connection to the lead. For example, the securing member 150 may be an adhesive material that secures the sheath 120 to the outer surface 110a of the lead 110. As a consequence of the securing member 150, that portion of the lead 110 covered by the sheath is not in contact with the patient's blood. Alternatively, the sheath 120 may be joined via a fusion bond of the polymeric material of the sheath to the polymeric coating of the lead 110. Of course these are exemplary securing members and should not be deemed to be an exhaustive list of preferred securing members 150. Again, this preferred configuration of the sheath 120 prevents the scar tissue 122 from contacting, adhering to, or constraining the sheath inner portion 124.

To extract the lead assembly 110, the suture 148 is removed at or near the proximal end 112 of the sheath 120. Thereafter, applying a tensile force to the proximal end 126 of the sheath inner portion 124 of a sufficient magnitude overcomes the holding force or connection of the frangible securing member 150 joining the sheath 120 and the lead assembly, and allows the sheath 120 to become separated from the outer surface 110a of the lead 110. Further extraction of the sheath inner portion 124 is accomplished by continued application of the tensile force at the proximal end 126 of the sheath inner portion which, in turn, applies a sufficient separating force of the sheath outer portion 142 to tear away from the scar tissue 122. In this manner, the distal ends 128, 144 of the sheath inner and outer portions, respectively, advance toward the proximal ends, 126, 146, respectively, and the sheath outer portion 142 continues to tear away from the scar tissue 122 in a generally longitudinal direction. The separated sheath outer portion 142 is separated from the scar tissue 122 and turns inwardly at the distal end 144 to become an extension of the sheath inner portion 120 that is longitudinally advanced within the remaining length of the sheath outer portion toward the proximal end 126. Thus, the sheath 120 "self-extracts", i.e., the sheath does not require a separate tool to separate or extract the lead 110 from the body passage. In this manner, the portion of the lead assembly 104 that is not at least partially encased by the scar tissue 122, i.e., the region covered by the sheath inner portion 124 and that portion of the lead 110 originally covered by the sheath inner portion, can be effectively removed from the vein 106. The tensile force on the sheath inner portion 120 is essentially transferred to the sheath outer portion 142 from or at the distal end 144 and progresses toward the proximal end 146 thereof. Due to the invaginated configuration of the sheath 120, the tensile force applied to the sheath inner portion 124 at the proximal end 126 results in application of a shearing force at the distal end 144 of the sheath outer portion 142 that separates the sheath from the scar tissue 122. The shearing force is concentrated at the distal end 144 of the invaginated sheath 120 and as the sheath outer portion 142 is separated from the scar tissue 122, the concentrated shearing force is longitudinally advanced from the distal end toward the proximal end 146 as the area of separation of the sheath outer portion from the scar tissue advances under the continued application of the tensile force (and resultant shearing force) from the distal end to the proximal end (see progressive separation of sheath illustrated in FIGS. 2-4). It will also be appreciated that the shearing force preferably acts over the entire circumference of the sheath outer portion 142 at the advancing distal end 144 in this embodiment of the present invention. Ultimately, the sheath 120 is separated from the scar tissue 122 and extracted from the vein 106.

Once the sheath 120 is self-extracted in this manner, the lead 110 may then be extracted or removed from the body passage/vein 106. After removal of the sheath 120, there is no scar tissue 122 retaining the lead assembly 104 and the lead 110 can be more easily extracted or removed from the heart 108 and vein 106.

Figure 5:
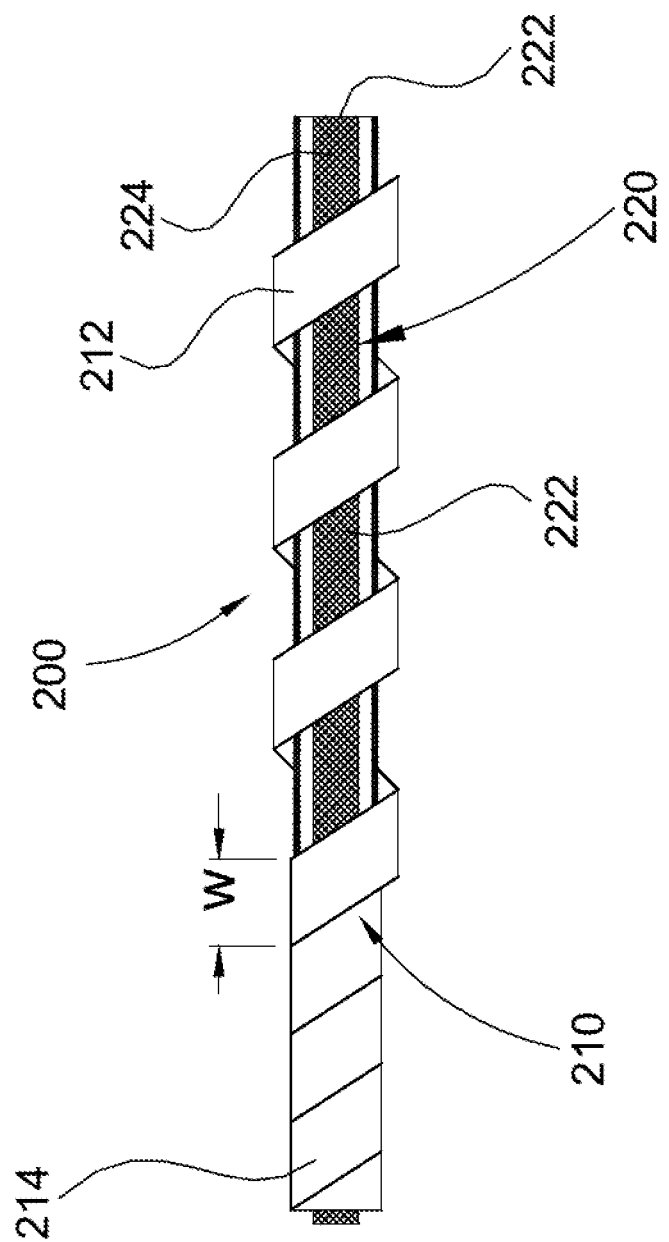
FIG. 5 is a view of modified form of sheath.

Reference is made to FIGS. 5-14 that illustrate alternative embodiments of features that facilitate removal of the lead, again, in these embodiments the features are self-extracting lead assemblies. Particularly, shown in FIG. 5 is a lead assembly 200 that includes an integrated self-extracting feature, namely, a helically or spirally wound sheath or band 210 having a first or proximal end 212 and a second or distal end 214. The lead assembly 200 includes a generally conventional lead 220 that has a conductive core 222 such as a conductive metal wire or the like, and a surrounding casing 224 formed of a material that is physiologically biocompatible with the human body such as a polymer material. Again, details of the conductive core 222 and casing 224 are well known in the art so that further description herein is unnecessary to a full and complete understanding of the present disclosure. Received over the outer casing 224 of the lead assembly is the sheath 210 that is secured at the proximal end 212 and the distal end 214 to opposite ends of the casing 224 of the lead assembly 200. In cross-section, the sheath 210 of FIG. 5 is generally planar, i.e. the sheath has a much greater width dimension than a thickness dimension so that the width portions spirally wrap around outer helical regions of the lead casing. As shown in the left-hand portion of FIG. 5, contiguous edges of the sheath abut one another to provide substantial enclosure of the entire outer surface of the lead assembly 200. This limits the potential for scar tissue to attach directly to the outer surface of the lead assembly and instead the scar tissue would attach/join to the sheath 210.

As represented in FIG. 5, when it is desired to extract the lead 220, the proximal end 212 of the sheath 210 is separated from the casing 224 of the lead. A tensile force applied to the sheath 210 separates the sheath from any surrounding scar tissue. As a result, the lead 220, and more particularly the casing 224, is no longer retained by the scar tissue of the body passage/vein (not shown) upon the tensile force separating the sheath and body passage. Further, the tensile force applied to the proximal end 212 of the sheath 210 provides a shearing action over the width "w" of the sheath so that the shearing action occurs over the helical extent of the sheath and components of the force are not distributed over the entire outer surface of the casing 224.

Figure 6:
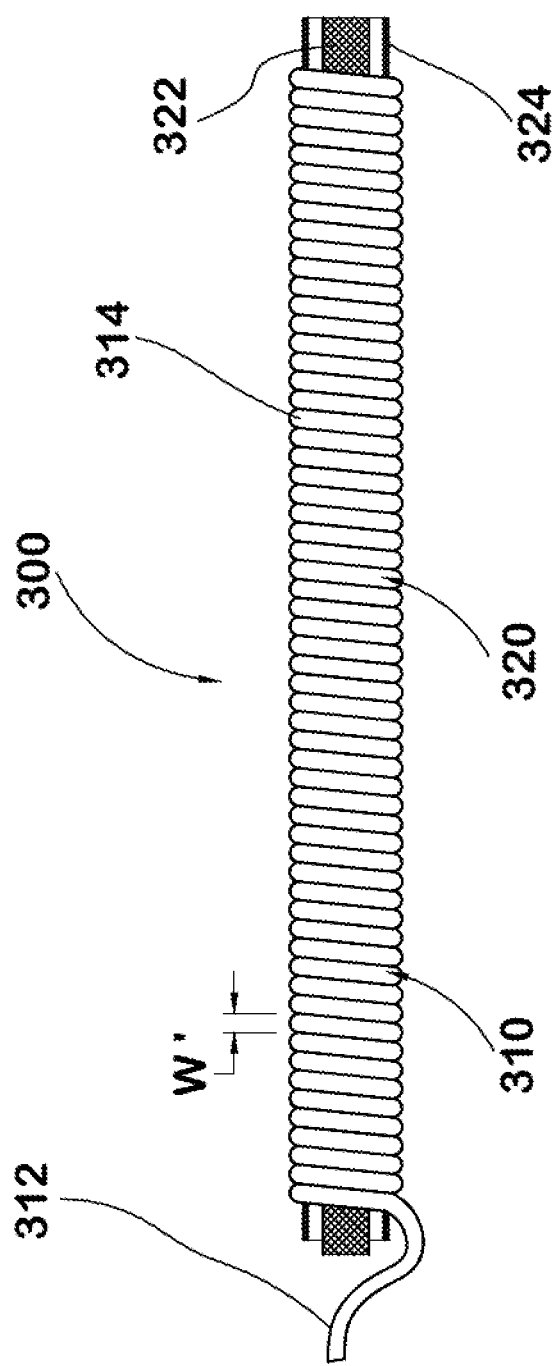
FIG. 6-8 are views of another type of self-extracting lead assembly having a helical sheath.
Figure 7:
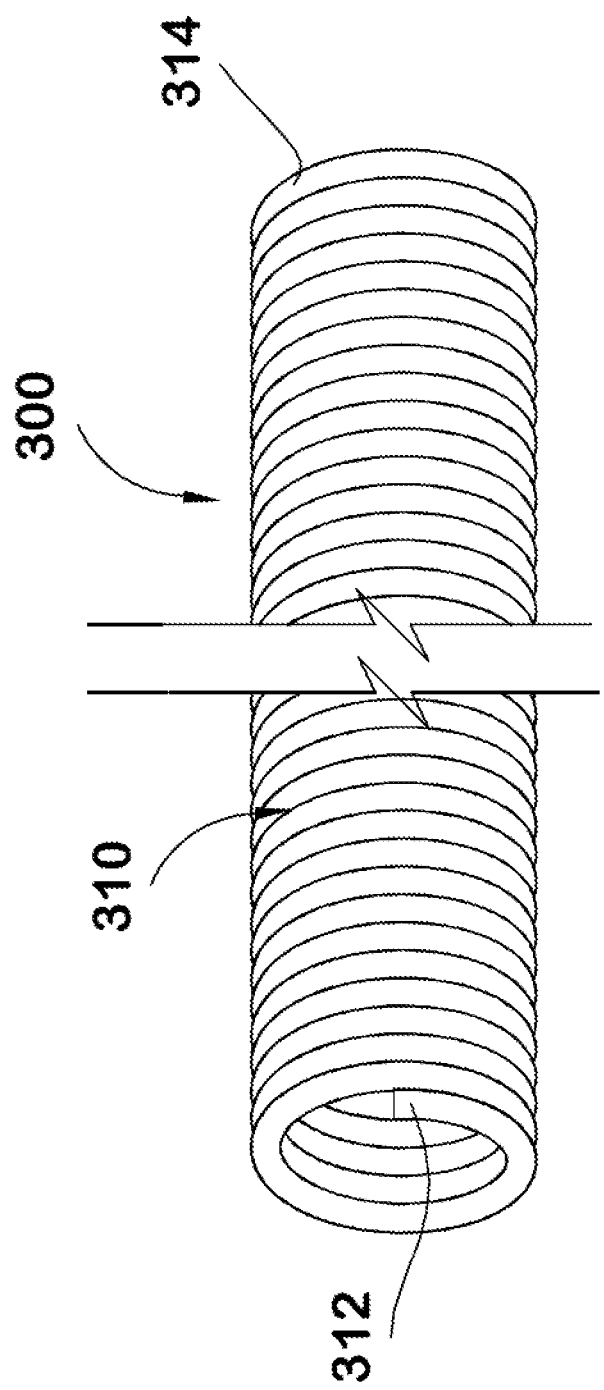
Figure 8:
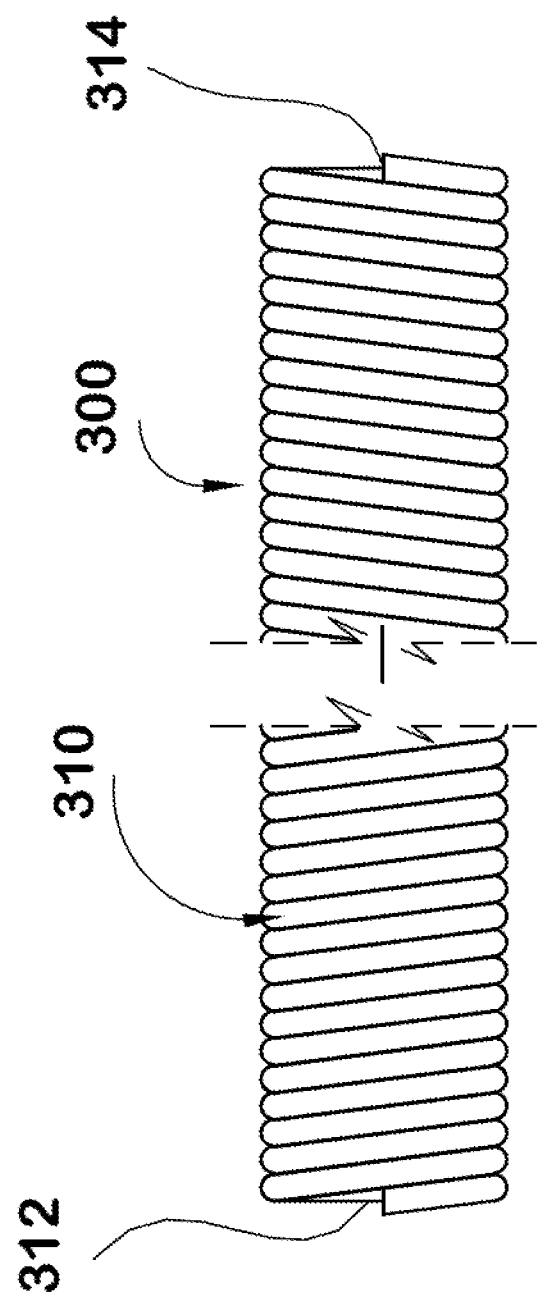

FIGS. 6-8 illustrate a lead assembly 300 that includes a helically or spirally wound sheath or wire 310 that is the feature that facilitates removal of the lead, and in this case, is a self-extracting feature. The sheath 310 has a first or proximal end 312 and a second or distal end 314. The lead assembly 300 includes a generally conventional lead 320 that has a conductive core 322 such as a conductive metal wire or the like, and a surrounding casing 324 that is formed of a material that is physiologically biocompatible with the human body such as a polymer material received over and encasing the conductive core. Again, details of the conductive core 322 and casing 324 are well known in the art so that further description herein is unnecessary to a full and complete understanding of the present disclosure. Received over the casing 324 is the helical sheath 310 that is secured at the proximal end 312 and the distal end 314 to opposite ends of the lead assembly 300, i.e., to an outer surface of the casing. In cross-section, the sheath 310 is generally cylindrical, i.e. the sheath has a generally circular outer conformation, and the sheath is spirally wrapped or wound around the outer surface of the lead casing 324. Contiguous edges of the sheath 310 abut one another when helically wrapped in a manner that encases and provides substantial enclosure of the entire outer surface of the lead assembly 300.

When it is desired to extract the lead 320, the proximal end 312 of the sheath 310 is separated from the casing 324 of the lead. A tensile force applied to the sheath 310 separates the sheath from any surrounding scar tissue. As a result, the lead 320, and more particularly the casing 324, is no longer engaged by or retained by the scar tissue of the body passage/vein (not shown). Further, the tensile force applied to the proximal end 312 of the sheath 310 provides a shearing action over the width "w" of the sheath so that the shearing action occurs over the helical extent of the sheath and components of the force are not distributed over the entire outer surface of the casing 324.

Figure 9:
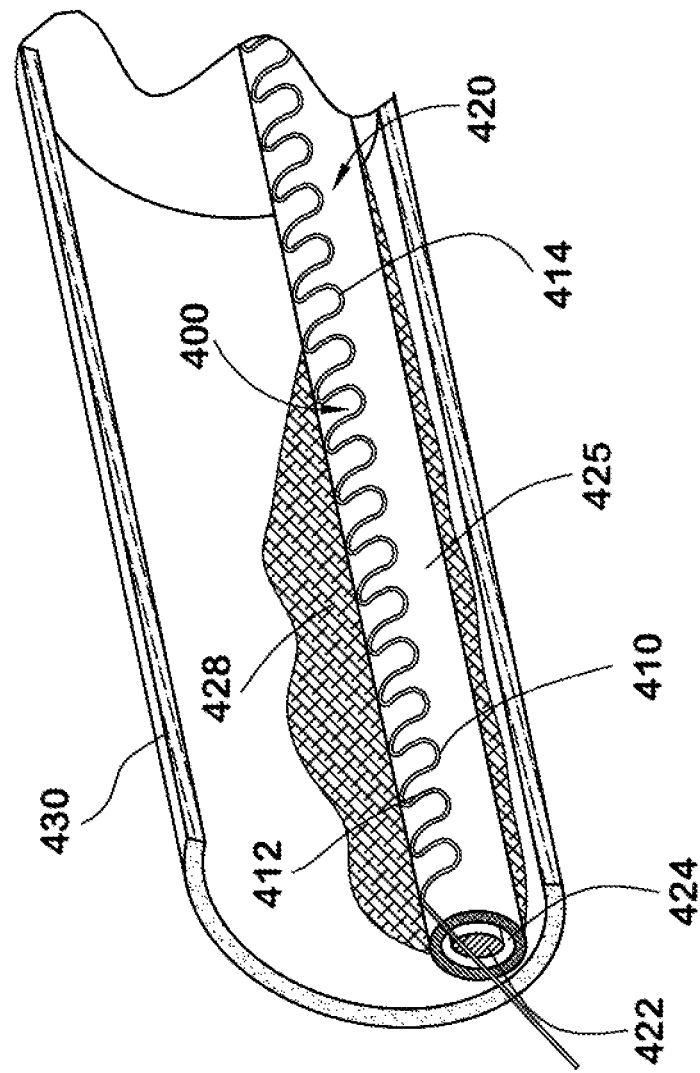
FIG. 9 is a perspective view of a version of a self-extracting lead assembly received in a body passage with scar tissue formed thereover.
Figure 10:
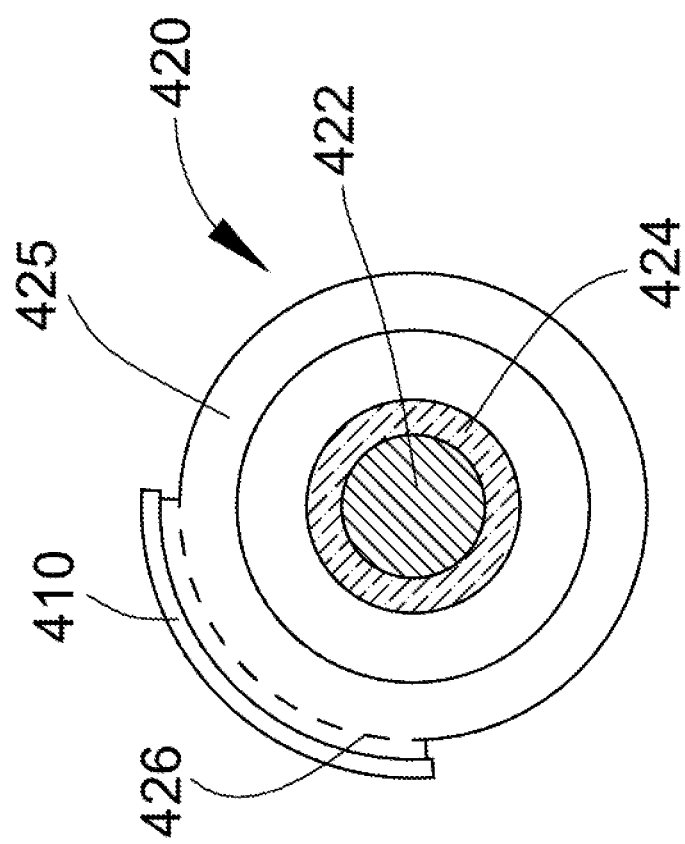
FIG. 10 is an end view of the FIG. 9 embodiment.
Figure 11:
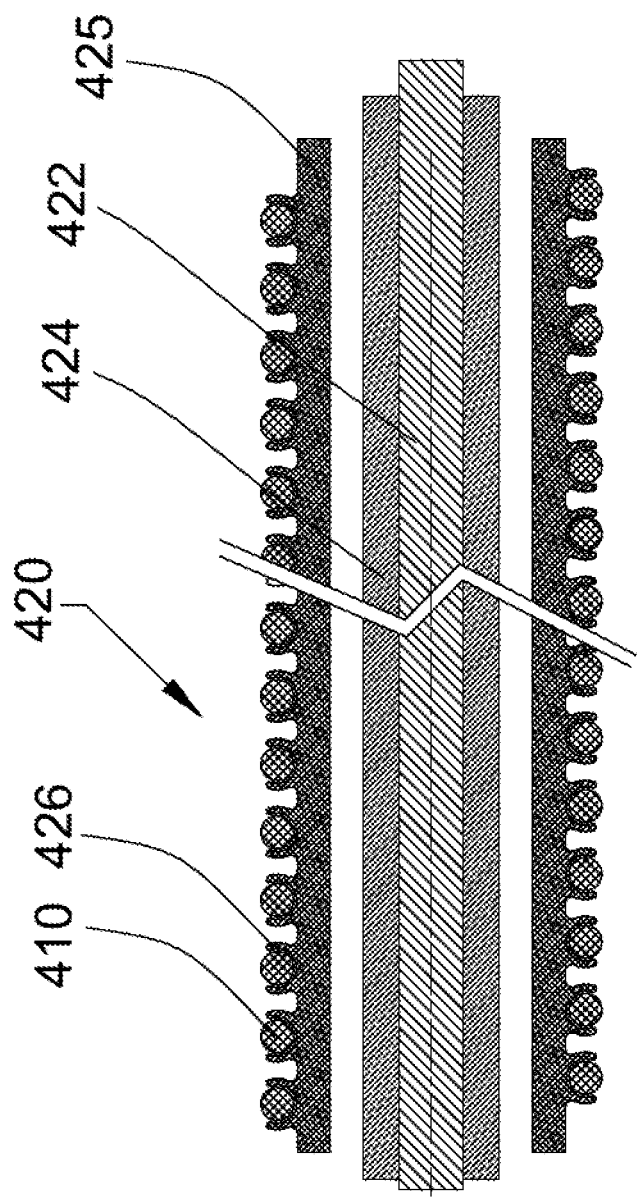
FIG. 11 is a longitudinal cross-sectional view of another self-extracting lead assembly of FIG. 6.

Similar features that facilitate extraction of the lead are incorporated into alternative embodiments illustrated in FIGS. 9-14. In FIGS. 9-11, lead assembly 400 includes a feature that facilitates extraction of a lead, specifically a wire 410 and modified casing that are integrated with the lead assembly. The wire 410 includes a first or proximal end 412 and a second or distal end 414. The lead 420 includes the conductive core 422 and casing 424. The perimeter of an outer casing 425 is slightly modified as perhaps best illustrated in FIGS. 10 and 11 to form or provide a serpentine groove or open channel 426 dimensioned to receive the self-extracting wire 410 therein. In certain embodiments the serpentine groove could alternatively be provided in casing 424 and outer casing 425 eliminated.

In selective embodiments the casing receiving the wire may be made thicker to permit the formation of the integral groove 426 that receives the outer perimeter of the wire 410 (see FIG. 11). The groove 426 has a depth and a substantially C-shape in cross-section that facilitates retention of the wire 410 therein. That is, the sidewalls of the groove 426 preferably receive a major portion (e.g., more than half of the cross-section of the wire) of the overall diameter of the wire 410 in order to adequately retain the wire in the groove. As scar tissue 428 from the body passage or vein 430 encloses over the lead 420, the proximal end 412 of the self-extracting wire 410 is placed under a tensile load and pulled from the groove 426 (the polymer material of the groove sidewalls being sufficiently flexible under the imposed force to allow the wire to move radially outward from retention in the groove) whereby the wire is used to separate the scar tissue 428 from the outer surface of the casing 424. The serpentine configuration of the wire 410 provides a shearing force that separates the scar tissue 428 from the lead assembly 400 and permits subsequent, easier removal of the lead 420.

Figure 12:
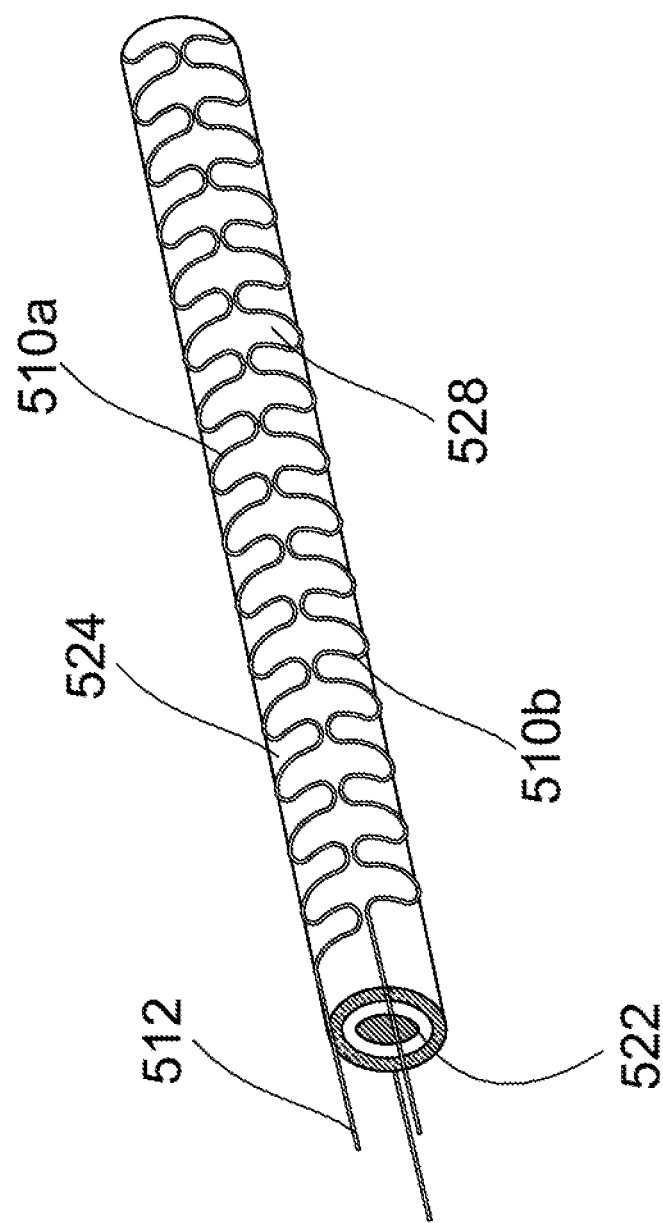
FIG. 12 is a perspective view of a similar version of the embodiment of FIG. 9.
Figure 13:
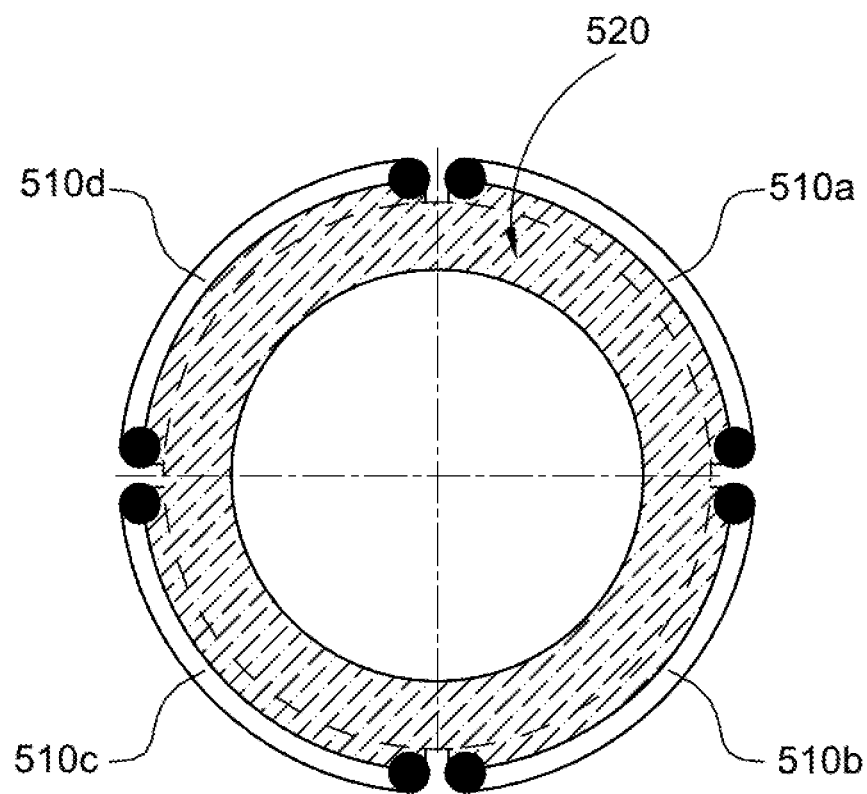
FIG. 13 is an enlarged cross-sectional view of the lead assembly of FIG. 12.
Figure 14:
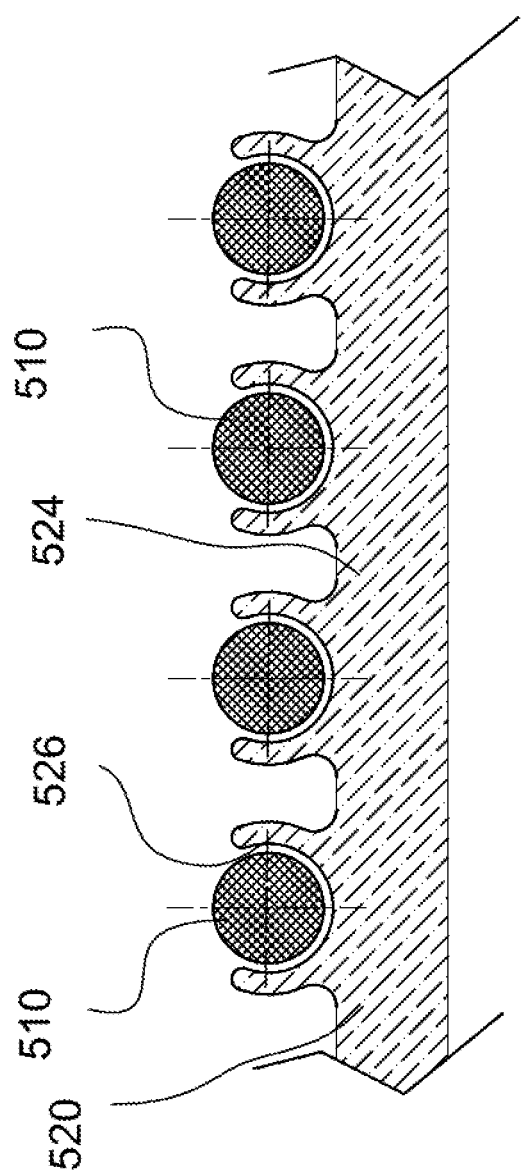
FIG. 14 is an enlarged detail view of a portion of the lead assemblies of FIGS. 11-13.

FIGS. 12-14 are similar to the embodiment of FIGS. 9-11. Lead assembly 500 includes a feature that facilitates extraction of the lead, namely a self-extracting wire 510 having a first or proximal end 512 and a second or distal end 514. Lead 520 includes a conductive core 522 and a casing 524. The casing 524 is slightly modified (relative to the arrangement of the embodiment of FIGS. 9-11) as perhaps best illustrated in FIGS. 13 and 14 to provide serpentine grooves 526 (FIG. 14) dimensioned to receive self-extracting wire portions 510 therein, i.e., four wire portions 510a-510d being illustrated. Of course a greater or lesser number of wire portions could be employed as desired without departing from the scope and intent of the present disclosure. As scar tissue 528 from the body passage or vein encloses over the lead 520, the proximal ends 512 of the self-extracting wire portions 510 are placed under a tensile load and used to separate the scar tissue 528 from the outer surface of the casing 524. The serpentine configuration of the wire 510 provides a shearing force that separates the scar tissue 528 from the lead assembly 500 and permits subsequent, easier removal of the lead 520.

Figure 15:
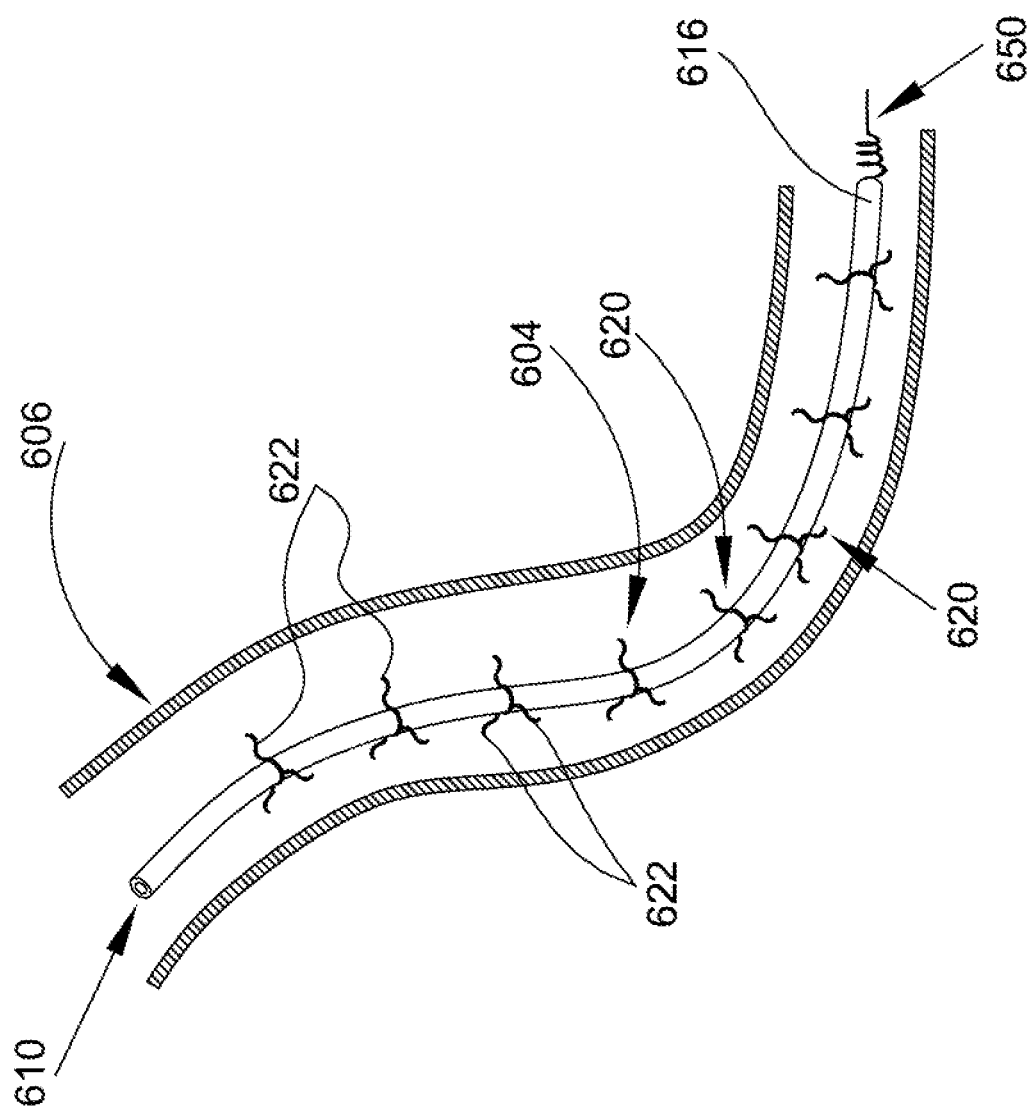
FIG. 15 is a schematic representation of another embodiment of lead assembly received in a vein and that is designed to facilitate removal or extraction of the lead without additional tools.
Figure 16:
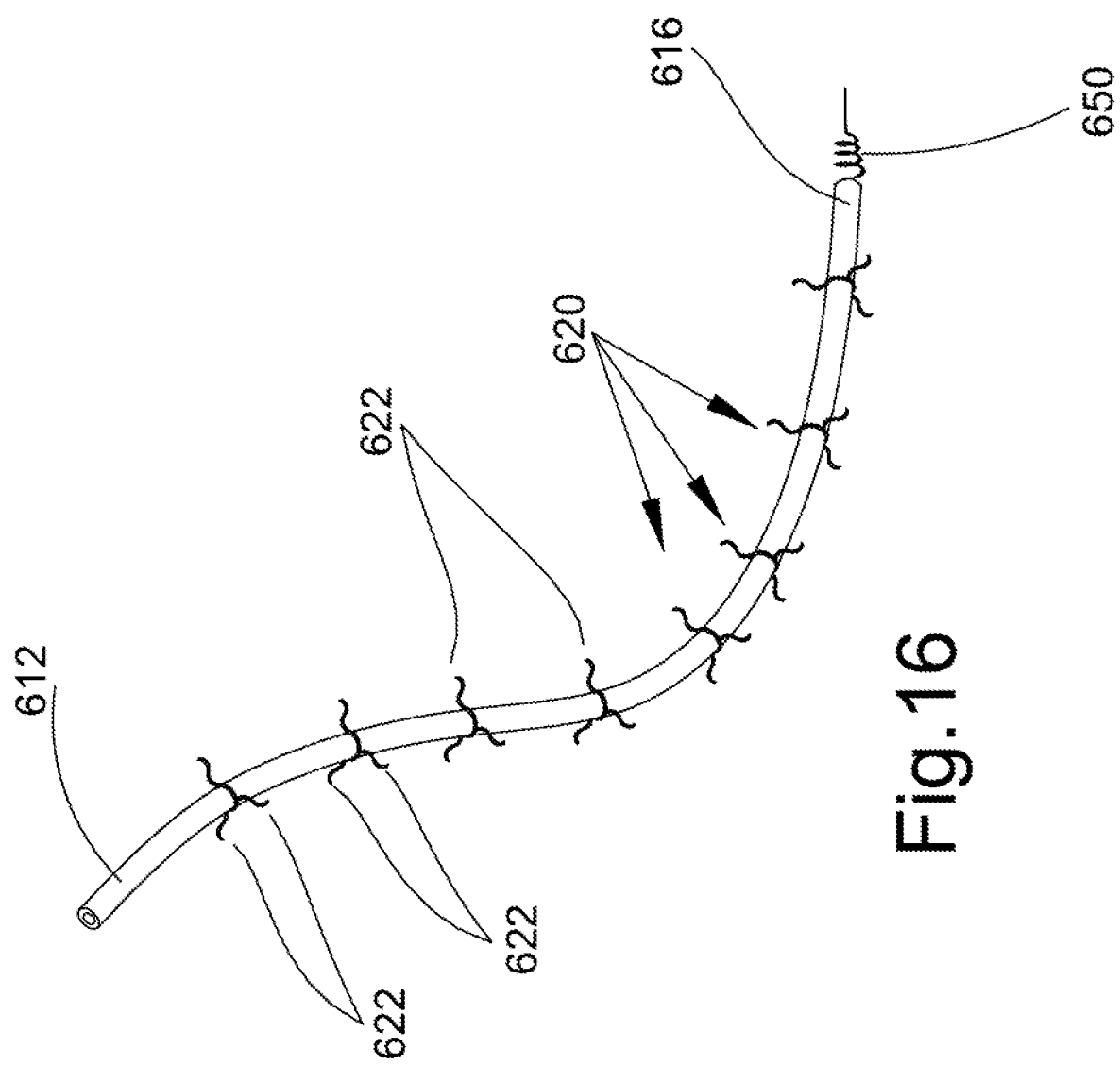
FIG. 16 illustrates the lead assembly of FIG. 15.
Figure 17:
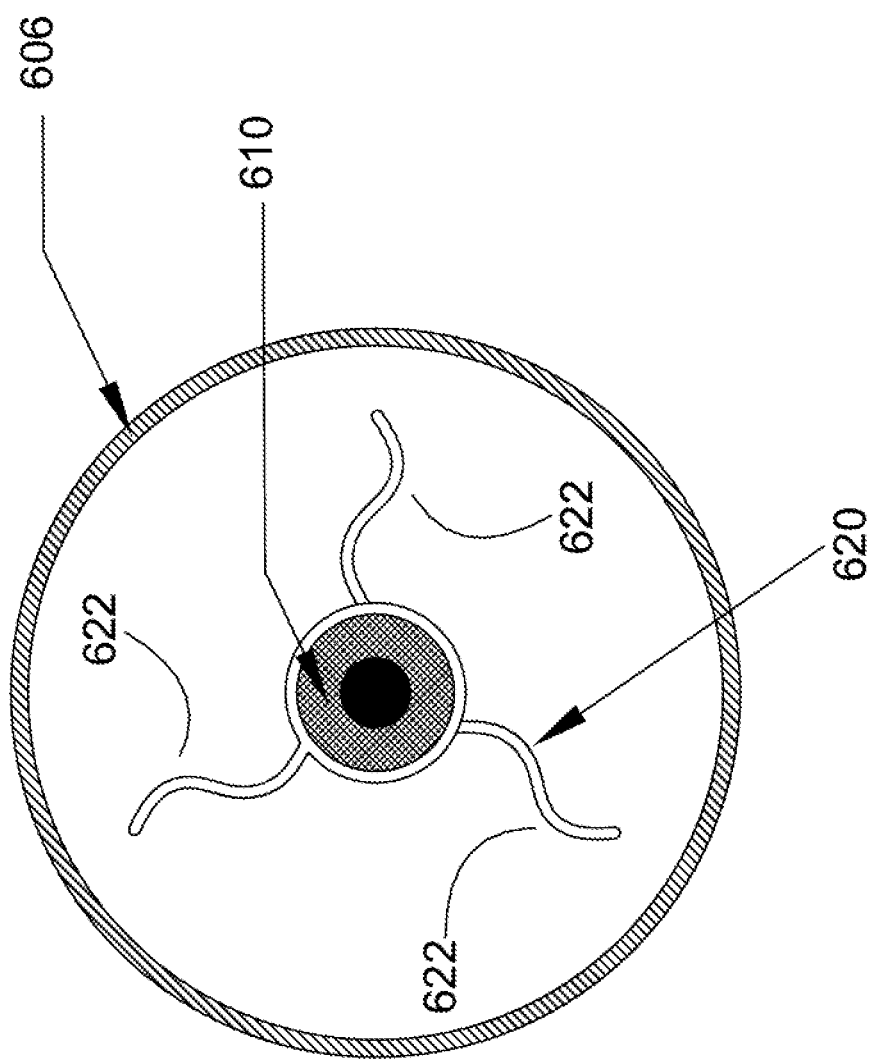
FIG. 17 is an enlarged cross-sectional view of the lead assembly of FIG. 15.

FIGS. 15-17 illustrate another embodiment of a lead assembly 604 received in a body passage such as vein 606. A first, proximal end 612 is disposed in axially spaced relation from the second, distal end 616, which includes a securing mechanism 650 to secure the lead to the myocardium (not shown). In this embodiment, lead 610 is a standard construction including the conductive core and a polymer casing. Secured to the polymer casing of the lead are a series of spoke assemblies 620 that include individual spokes 622 that extend radially outward from the longitudinal extent of the lead 610. For example, at axially spaced locations, each spoke assembly 620 includes three or more spokes 622 located in circumferentially spaced relation about the perimeter of the lead 610. The spokes 622 have a radial length whereby if the lead 610 were centered in the vein, the spokes would not make contact with the inner wall of the vein. Although a clearance between the outer, terminal end of the spoke and the inner wall of the body passage is desirable, it is not required. If there is contact between the spoke and the inner wall of the vein, the area of contact is minimized. The vein is typically a curvilinear path, the twists and turns result in the lead 610 making contact with inner surface of the vein at one or more spaced locations. These locations are where scar tissue is likely to initially form because of contact with the body passage. Thus, the spokes 622 limit the surface area of the scar tissue that forms over the lead 610. That is, preferably the spokes 622 are covered with scar tissue rather than a remainder of the outer surface of the lead 610. The spokes 622 are also preferably flexible so that fixed contact with the inner surface of the body passage is minimized as blood flows through the vein. It is intended that the spokes 622 have a generally spring-like action so as to deflect in response to each pulse of blood flow through the vein and have a self-restoring action that urges the spokes toward their original position. Different versions of the spokes 622 are contemplated. For example, the spoke assembly 620 may be fixed against rotation about the lead 610 while the flexible spokes 622 still extend radially outward. In another version, the spoke assembly 620 may be rotatable like a turbine, i.e. rotationally movable about the outer surface of the lead 610. In still another version, the spokes 622 may have some radial rigidity (e.g., the spokes are torsionally rigid) but are deflectable in an axial direction, i.e., outer terminal ends of each spoke tangentially engage the inner surface of the vein.

In summary, a first solution or first embodiment, includes a cover or sheath that surrounds the lead. The sheath has a hollow, tubular configuration that is turned back upon itself, i.e., the sheath is invaginated. The overall length of the sheath is increased almost two-fold because of the invaginated form of the sheath; however, the sheath is preferably configured so that the first, inner portion is used as the actuating member for extracting the sheath and thereby the lead contained in the sheath. The sheath has outwardly facing or outer surface portions thereof that face the inner surface of the body passage/vein. The outer surface portions of the outer portion of the sheath are likely those regions of the lead that are at least partially covered by scar tissue and that make it difficult to easily extract the lead from the body passage. By folding the sheath upon itself, the inner portion of the invaginated sheath is pulled in an axial direction relative to the outer portion. An interconnecting or fold-back region joins the inner and outer portions of the sheath at a location originally situated adjacent a terminal, distal end of the lead, e.g., adjacent the heart. As the inner portion is axially advanced relative to the outer portion, the outer portion receives the shearing force provided by the applied tensile force and separates the sheath from the scar tissue.

The integrated feature or component of other embodiments that facilitate extraction of the lead include a helical, serpentine, or wave-like sheath or wire-like component (e.g., having a diameter of approximately 0.005" to about 0.010", although this diameter may vary as development of the device continues and so the dimension should not be deemed limiting) that is received on the outer surface of the lead, or partially or wholly encompassed in a thin layer adjacent the outer surface of the lead. If received or secured to the outer surface of the lead, the serpentine member can be adhesively and/or mechanically captured in whole or in part to the outer surface. In still another arrangement, the integrated feature that facilitates extraction of the lead is a spoke assembly in which individual spokes limit the amount of scar tissue that may form over the lead due to the flexible nature of the spokes.

As a result of this modified lead, the integral extraction-enhancing component is an integrated structure or feature of the inserted lead. If it is later determined that the lead must be extracted, exerting a force on the serpentine member provides a separation/cutting action between the external surface of the lead and the surrounding tissue. In essence, the serpentine member is "uncoiled" when pulled, and becomes more linear as the pulling or tensile force on the lead separates the lead from the tissue.

In one embodiment, the serpentine member extends over a substantial external surface of the lead. Alternately, it is contemplated that the serpentine member can be a series of serpentine members that cover partial, circumferential regions of the external surface of the lead, e.g., the serpentine member can be provided as separate serpentine member portions that each extend over individual circumferential portions such as quadrants (i.e., four serpentine members—one for each quadrant) along the external surface of the lead. Of course the external serpentine member portions need not be the same size, regular/periodic, nor is it required that the serpentine member(s) have the same pattern (regular or irregular, constant or differing pitch, etc.).

Figure 18:
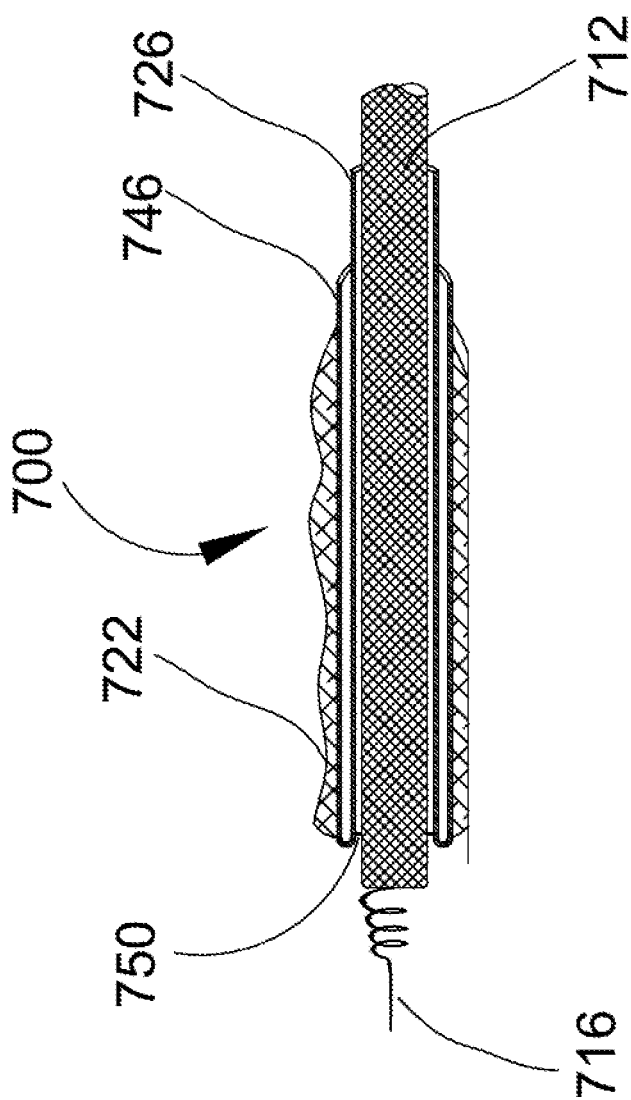
FIG. 18 is an enlarged longitudinal, cross-sectional view of a modified lead assembly that incorporates a frangible seal between the inner diameter of the sheath and the outer surface of the lead.
Figure 19:
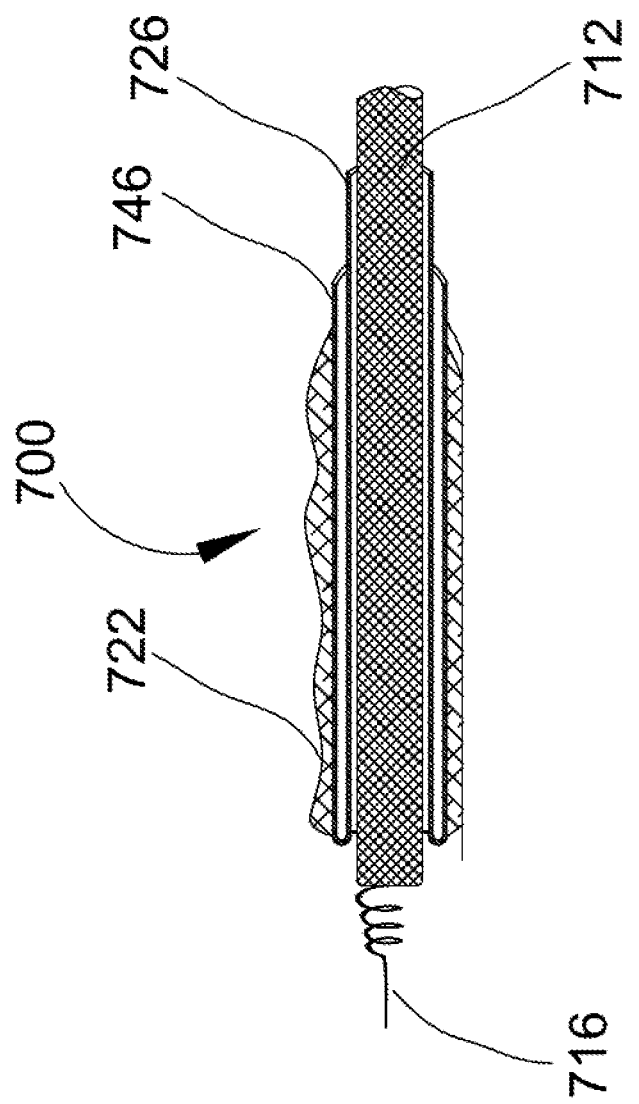
FIG. 19 is a further enlarged cross-sectional view of another embodiment illustrating formation of the diameter of the lead being greater than the inner diameter of the sheath so that the sheath imposes a radially inward compression force on the outer surface of the lead.
Figure 20:
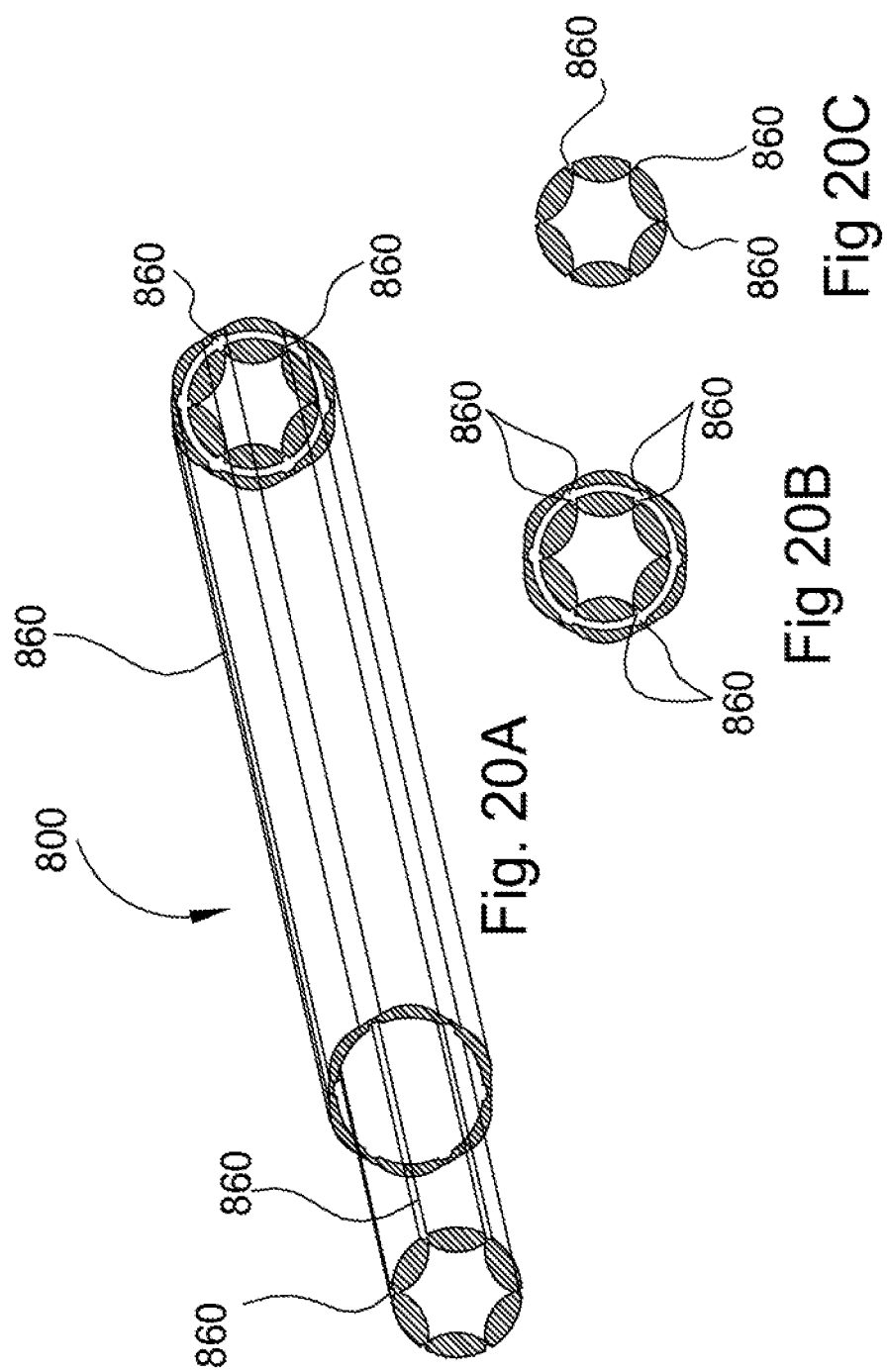
FIGS. 20A-20C and 21A-21C, show another embodiment where score lines are added to the sheath to allow segmented removal of the sheath.
Figure 21:
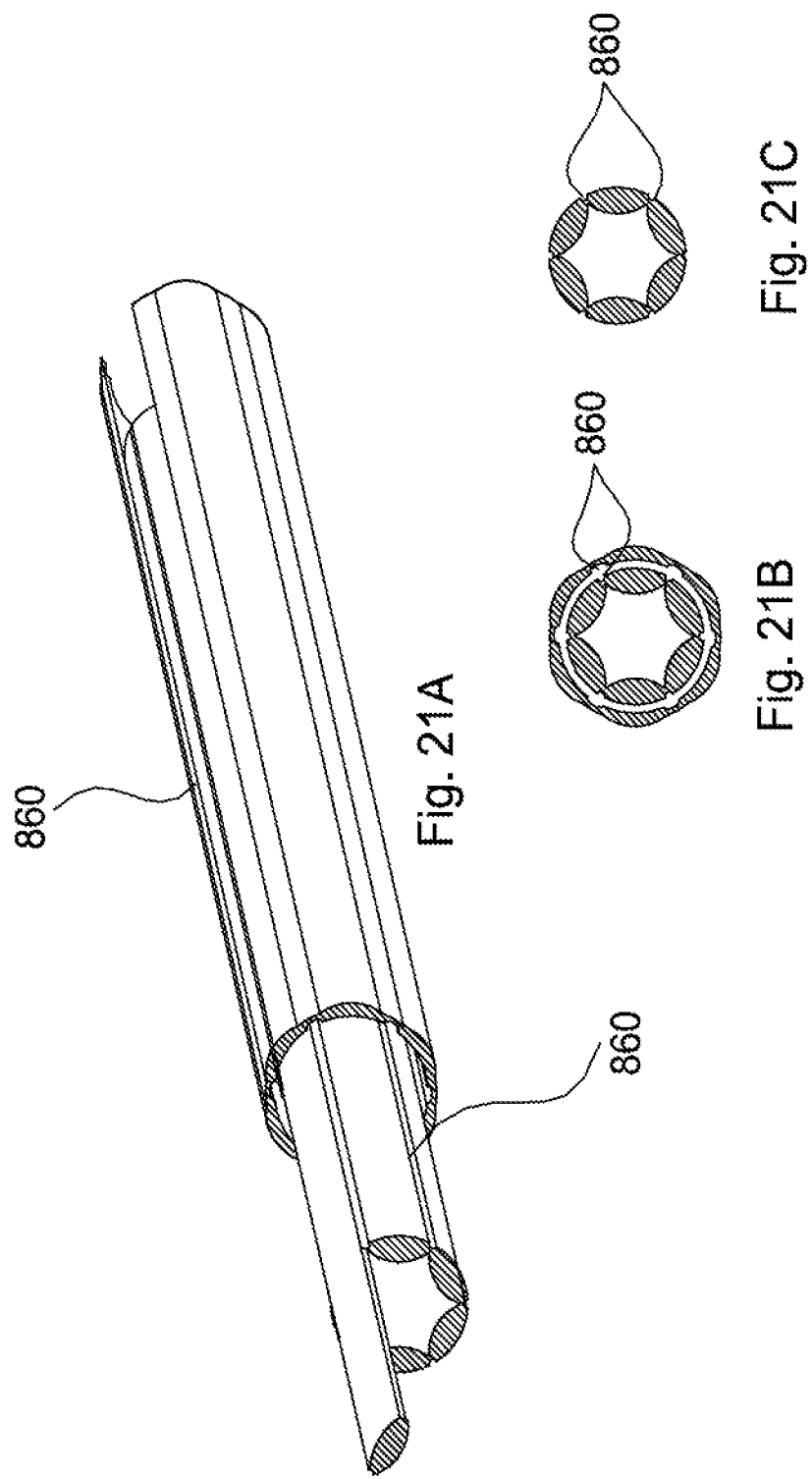

In FIGS. 18-19, lead assembly 700 is modified by including a seal 750 that extends in annular fashion between the outer surface of the lead and the inner surface of the sheath. Preferably, the seal 750 is a thin wall that is frangible, i.e., may be selectively pierced or broken in response to a predetermined force. Thus, the seal 750 prevents blood from entering the gap between the lead and the sheath, and is broken during the removal process as described above in connection with the other embodiments. In FIG. 19, the sheath inner portion is closely received on the outer surface of the lead so that a separate seal is not necessary since there is no radial gap between the outer surface of the lead and the inner surface of the sheath.

FIGS. 20A-20C and 21A-21C show a lead assembly 800 in which the sheath is modified by incorporating a series of score lines 860 that divide the sheath into segmented portions. Here, the score lines 860 are shown as being equally spaced about the sheath, and preferably extend along the entire longitudinal extent of the sheath. The score lines 860 are shown in parallel, linear arrangement although it will be appreciated that other configurations of the score lines may be used with equal success. In this manner, the removal force of the invaginated sheath may be focused on a segmented portion that only extends over a portion of the circumference or discrete annular region between the lead and the sheath. Depending on the amount of scar tissue, for example, that may have developed, the segmented portions may facilitate removal of the sheath, and ultimately removal of the lead assembly.

Figure 22:
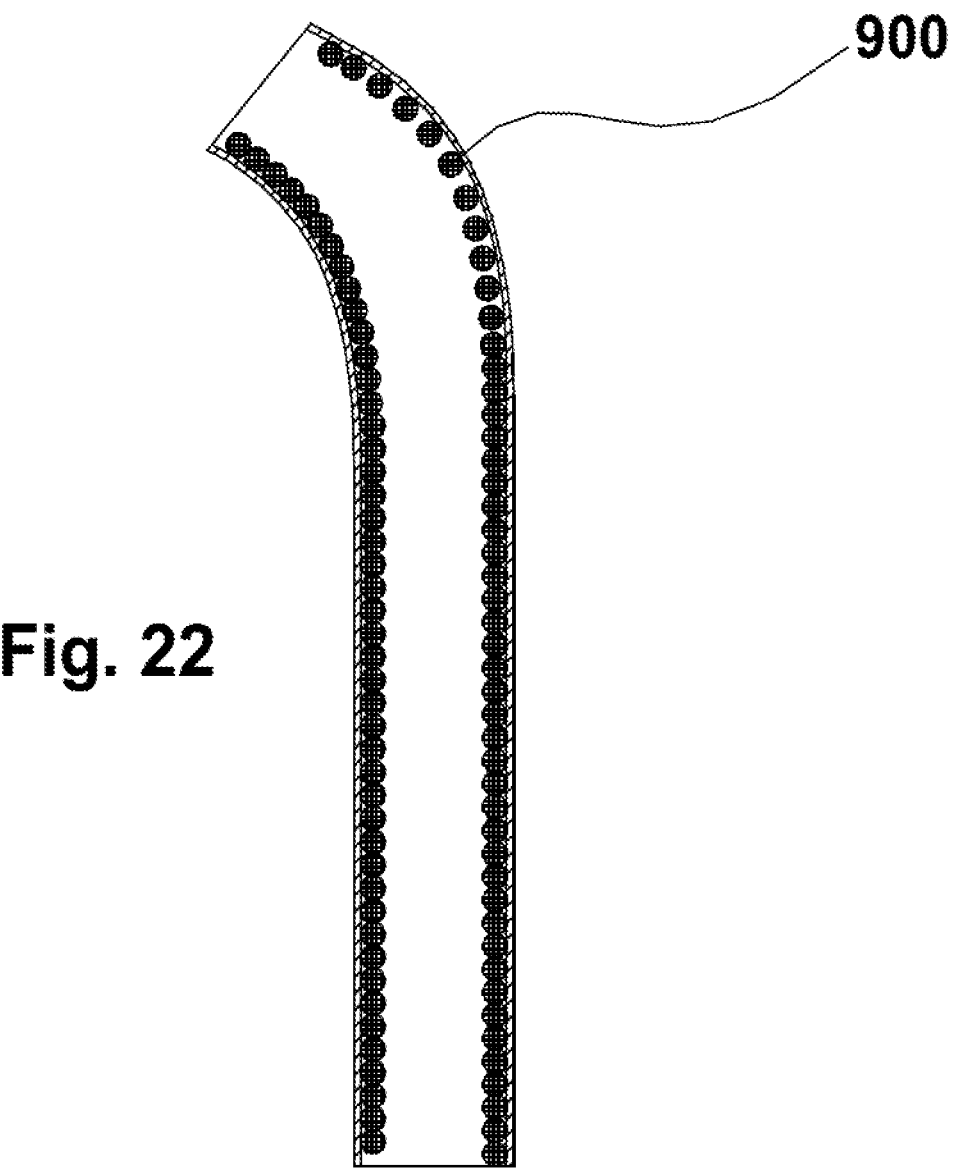
FIG. 22 illustrates a helical spring-like coil received on the lead and inclusion of the sheath over the outer diameter of the coil.

In FIG. 22, where a lead assembly 900 is bent, the spring-like coil casing can develop gaps between adjacent coil turns (note upper right-hand corner of FIG. 22). To prevent intrusion of blood and scar tissue into these gaps or region, the sheath 980 is preferably provided over the coils.

Figure 23:
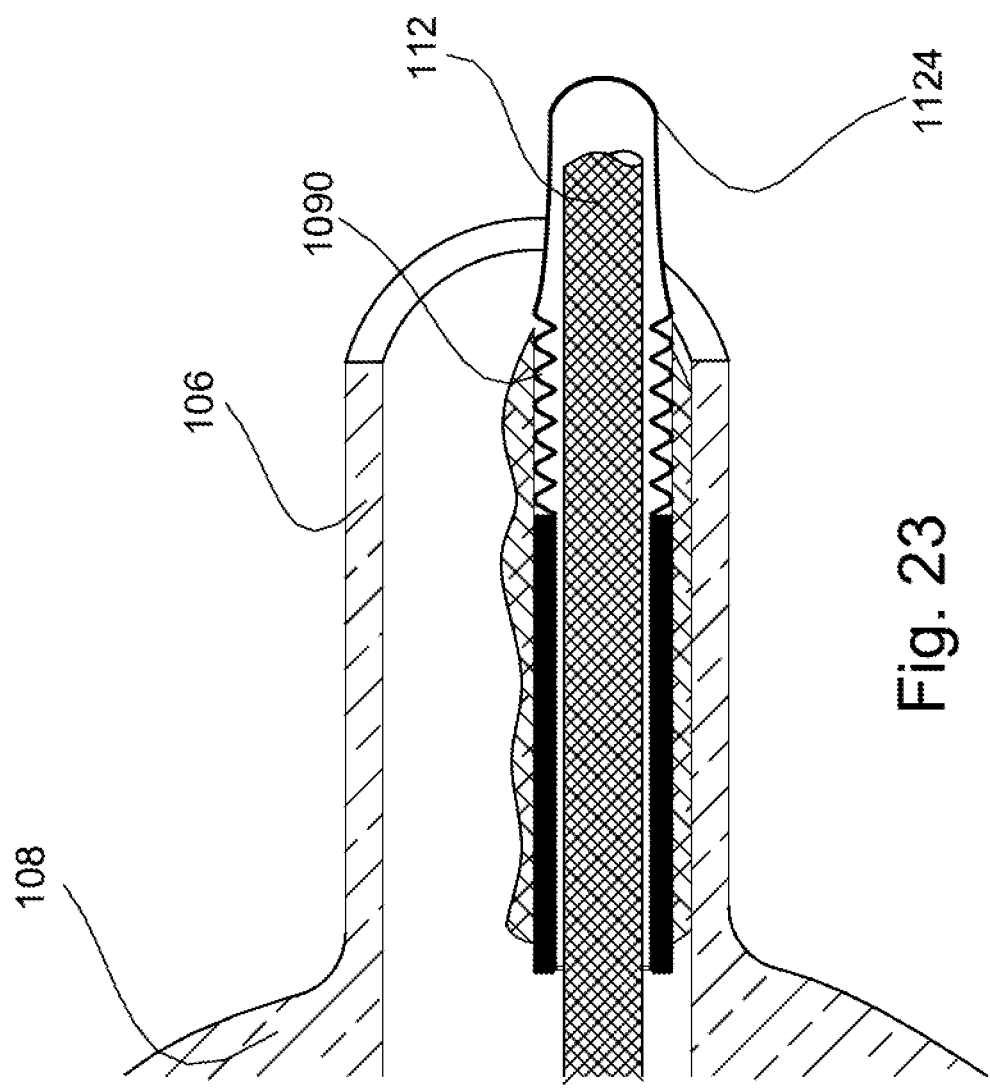

FIGS. 23-24 illustrate how the sheath may adopt a pleated or bellows type configuration. The individual pleats 1090 are normally collapsed or disposed closely adjacent one another as shown in the upper portion of FIG. 23. When the tensile or extracting force is imposed (as illustrated in FIG. 24), the pleats unfurl from their compressed, adjacent configuration and expand into a spaced configuration that forms a sawtooth gap between adjacent pleats of the of the bellows. Again, one skilled in the art will appreciate that the bellows-like sheath serves to limit intrusion of blood or scar tissue by preventing blood or scar tissue from passing radially between the individual pleats.

FIGS. 25A-25B, 26A-26B, and 27A-27B show a two-part sheath structure in which the two parts or portions are subsequently joined together to form a single sheath. Instead of a single tube, two flexible tubes are joined together. Specifically, in FIGS. 25A-25B, sheath inner portion 1100 has a distal end 1102 that extends axially beyond a sheath outer portion 1104, specifically beyond a distal end 1106. The distal end 1102 is thus turned radially outward (FIG. 25B) and then joined (e.g., secured together or fused) so that the joinder region is positioned on the sheath outer portion. In the embodiment of FIGS. 26A-26B, the sheath inner portion 1110 has a distal end 1112 that terminates before reaching a sheath outer portion 1114, specifically does not axially extend to a distal end 1116 of the sheath outer portion. The distal end 1116 of the sheath outer portion 1114 is thus turned radially inward (FIG. 26B) and then joined (e.g., secured together or fused so that the joinder region is positioned within the sheath outer portion. It is also comtemplated that the two components that form sheath inner and outer portions would have the same length and would be joined (e.g., fused) at the terminal, distal ends thereof (FIG. 27).

FIG. 28 is yet another embodiment where the sheath is modified. If the axial force imposed on the sheath to separate the sheath outer portion from the scar tissue results in too much radial contraction of the flexible material used to form the sheath, the structure of the sheath can be modified. Particularly, the material that forms sheath 1120 must still be sufficiently flexible to allow the sheath to be turned inside out, i.e., invaginated, however, reinforcing components 1122 are incorporated therein. The reinforcing components are flexible but are axially inextendible relative to the first flexible material. A preferred reinforcing component 1122 is formed by reinforcing cords that are spaced apart. For example, the reinforcing cords 1122 are circumferentially spaced apart in the sheath material 1120.

This written description uses examples to describe the disclosure, including the best mode, and also to enable any person skilled in the art to make and use the disclosure. Other examples that occur to those skilled in the art are intended to be within the scope of the invention if they have structural elements or process steps that do not differ from the same concept, or if they include equivalent structural elements or process steps with insubstantial differences.

It is claimed:

1. A lead assembly received through an associated body passage, the lead assembly comprising:
    an electrically conductive lead dimensioned for receipt in the associated body passage, the lead having an outer surface that extends between a proximal end and a distal end; and
    an integrated feature that facilitates extraction of the lead from the associated body passage, wherein the integrated feature that facilitates extraction includes a sheath dimensioned for receipt in the associated body passage and received over the lead, the sheath including
        (i) a first portion extending from adjacent the proximal end to adjacent the distal end of the lead, the first portion having an inner, first surface interfacing with the lead outer surface and the first portion further having an outer, second surface facing radially outward from the lead outer surface, and
        (ii) a second portion extending from adjacent the distal end to adjacent the proximal end of the lead, the second portion having an inner, first surface received over and abutting the outer, second surface of the first portion, and the second portion further having an outer, second surface abutting with an inner surface of the associated body passage that receives the lead therein.

2. The lead assembly of claim 1 wherein the first and second portions of the sheath are an integral, one-piece, continuous component.

3. The lead assembly of claim 1 wherein the outer surface of the first portion of the sheath is a continuous extension of the inner surface of the second portion of the sheath.

4. The lead assembly of claim 3 wherein the inner surface of the first portion of the sheath is a continuous extension of the outer surface of the second portion of the sheath.

5. The lead assembly of claim 1 wherein the inner surface of the first portion of the sheath is a continuous extension of the outer surface of the second portion of the sheath.

6. The lead assembly of claim 1 wherein the sheath includes a folded region where the second portion is a continuous extension of the first portion and the second portion is folded over the first portion.

7. The lead assembly of claim 1 wherein the sheath is formed of a first flexible material that includes reinforcing components incorporated therein, the reinforcing components are flexible and axially inextendible relative to the first flexible material.

8. The lead assembly of claim 7 wherein the reinforcing components include reinforcing cords that are spaced in the sheath.

9. The lead assembly of claim 1 wherein the sheath is an elongated tube formed by joining the first and second portions together.

10. The assembly of claim 9 wherein the first and second portions are the same length before being joined.

11. The assembly of claim 9 wherein the first and second portions are different lengths before being joined.

12. The assembly of claim 1 wherein the sheath is dimensioned for receipt in the associated body passage and received over the lead, and the assembly including a frangible seal located between the sheath and the lead at the distal end of the lead.

13. The assembly of claim 1 wherein the sheath is dimensioned for receipt in the associated body passage and received over the lead, the sheath including at least one score line that divides the sheath into segments.

14. The assembly of claim 13 wherein the at least one score line includes multiple score lines.

15. The assembly of claim 14 wherein the score lines are equi-spaced on the sheath.

16. The assembly of claim 14 wherein the score lines are parallel to one another.

17. The assembly of claim 16 wherein the score lines are linear.

18. The assembly of claim 14 wherein the score lines are linear.

19. The assembly of claim 13 wherein the at least one score line extends along an entirety of a longitudinal length of the sheath.

20. A lead assembly for in-vivo insertion in a body passage comprising:
  a signal lead sized and configured for insertion in the body passage having an outer surface extending between a proximal end and a distal end; and
  a sheath extending over the lead having an inner layer received over and contacting the lead outer surface and an outer layer received over the inner layer, the outer layer sized and configured for receipt in the body passage, wherein the inner layer is connected to the outer layer at the distal end by an annular fold.

21. The assembly of claim 20 wherein the assembly is removable from the body passage by application of tensile force to the inner layer at the proximal end, whereupon the annular fold moves progressively toward the proximal end and the sheath and lead are removed.

22. The assembly of claim 20 wherein the sheath inner layer and outer layer are formed of a flexible material.

23. The assembly of claim 20 wherein the inner and outer layers have a plurality of tension members disposed in one of (i) thereon and (ii) embedded therein.

* * * * *